United States Patent
Uehara et al.

(10) Patent No.: US 10,687,771 B2
(45) Date of Patent: Jun. 23, 2020

(54) X-RAY DIAGNOSTIC APPARATUS COMPRISING A POSITION SPECIFYING UNIT AND A CONTROL UNIT

(71) Applicant: Toshiba Medical Systems Corporation, Otawara-shi (JP)

(72) Inventors: Hisayuki Uehara, Otawara (JP); Takeo Matsuzaki, Nasushiobara (JP); Akio Tetsuka, Shioya (JP); Jun Sakakibara, Otawara (JP); Katsuie Ikawa, Nasushiobara (JP); Masashi Hirasawa, Nasushiobara (JP); Keisuke Sugawara, Otawara (JP)

(73) Assignee: Canon Medical Systems Corporation, Otawara-shi (JP)

(*) Notice: Subject to any disclaimer, the term of this patent is extended or adjusted under 35 U.S.C. 154(b) by 733 days.

(21) Appl. No.: 14/953,197

(22) Filed: Nov. 27, 2015

(65) Prior Publication Data

US 2016/0074000 A1    Mar. 17, 2016

Related U.S. Application Data

(63) Continuation of application No. PCT/JP2014/064634, filed on Jun. 2, 2014.

(30) Foreign Application Priority Data

May 31, 2013  (JP) .................. 2013-115579

(51) Int. Cl.
*A61B 6/00* (2006.01)
*A61B 6/04* (2006.01)

(52) U.S. Cl.
CPC .......... *A61B 6/4441* (2013.01); *A61B 6/4405* (2013.01); *A61B 6/547* (2013.01);
(Continued)

(58) Field of Classification Search
CPC ....... A61B 6/04; A61B 6/0407; A61B 6/0457; A61B 6/44; A61B 6/4405; A61B 6/4411;
(Continued)

(56) References Cited

U.S. PATENT DOCUMENTS 6,131,690 A * 10/2000 Galando .............. A61B 6/4405
                                                   180/19.1
6,196,715 B1 * 3/2001 Nambu .................... A61B 6/00
                                                   378/11
(Continued)

FOREIGN PATENT DOCUMENTS

JP    2009-22602     2/2009
JP    2009-233252   10/2009
(Continued)

OTHER PUBLICATIONS

International Search Report dated Jun. 24, 2014 in PCT/JP2014/064634 filed Jun. 2, 2014 (with English translation).
(Continued)

*Primary Examiner* — Allen C. Ho
(74) *Attorney, Agent, or Firm* — Oblon, McClelland, Maier & Neustadt, L.L.P.

(57) ABSTRACT

An X-ray diagnostic apparatus according to one embodiment comprises an X-ray tube, an X-ray detector, a holding mechanism, position specifying circuitry and control circuitry. The X-ray detector detects the X-ray which has been generated by the X-ray tube and has passed through an object placed on a top of a bed movable in an examination room. The holding mechanism holds the X-ray tube and the X-ray detector, and movable in the examination room. The position specifying circuitry specifies a position of the holding mechanism in the examination room and a position of the bed in the examination room. The control circuitry controls the holding mechanism in order to change a position and angle of the holding mechanism based on the
(Continued)

US 10,687,771 B2

Page 2 position of the holding mechanism and the position of the bed.

13 Claims, 19 Drawing Sheets

(52) U.S. Cl.
CPC .............. *A61B 6/04* (2013.01); *A61B 6/0407* (2013.01); *A61B 6/4452* (2013.01); *A61B 6/4458* (2013.01); *A61B 6/4464* (2013.01)

(58) Field of Classification Search
CPC ... A61B 6/4429; A61B 6/4435; A61B 6/4441; A61B 6/4452; A61B 6/4458; A61B 6/4464; A61B 6/547
USPC .................... 378/189, 196–198, 205, 209
See application file for complete search history.

(56) References Cited

U.S. PATENT DOCUMENTS

| | | | | |
|---|---|---|---|---|
| 6,200,024 | B1 * | 3/2001 | Negrelli | A61B 6/4233 378/196 |
| 6,234,672 | B1 * | 5/2001 | Tomasetti | A61B 6/4405 378/114 |
| 6,334,708 | B1 * | 1/2002 | Kosugi | A61B 6/0457 378/197 |
| 6,374,937 | B1 * | 4/2002 | Galando | A61B 6/4405 180/19.1 |
| 6,409,381 | B1 * | 6/2002 | Siebenhaar | H05G 1/02 378/114 |
| 6,412,978 | B1 * | 7/2002 | Watanabe | A61B 6/105 378/196 |
| 6,428,206 | B1 * | 8/2002 | Watanabe | A61B 6/4233 378/197 |
| 6,435,715 | B1 * | 8/2002 | Betz | A61B 6/4458 378/197 |
| 6,508,586 | B2 * | 1/2003 | Oota | A61B 6/032 378/194 |
| 6,609,826 | B1 * | 8/2003 | Fujii | A61B 6/12 378/197 |
| 6,614,871 | B1 * | 9/2003 | Kobiki | A61B 6/035 250/522.1 |
| 6,764,217 | B2 * | 7/2004 | Yasuda | A61B 6/08 378/196 |
| 6,814,490 | B1 * | 11/2004 | Suhm | A61B 6/4405 378/195 |
| 6,869,217 | B2 * | 3/2005 | Rasche | A61B 6/4441 378/193 |
| 7,016,457 | B1 * | 3/2006 | Senzig | A61B 6/032 378/116 |
| 7,034,492 | B2 * | 4/2006 | Curtis | A61B 6/102 318/560 |
| 7,197,112 | B2 * | 3/2007 | Maschke | A61B 6/4429 378/116 |
| 7,246,943 | B2 * | 7/2007 | Gotoh | A61B 6/4014 378/196 |
| 7,261,464 | B2 * | 8/2007 | Noda | A61B 6/4441 378/195 |
| 7,300,204 | B2 * | 11/2007 | Gotoh | A61B 6/4441 378/197 |
| 7,502,174 | B2 * | 3/2009 | Jensen | A61B 6/04 348/370 |
| 7,764,765 | B2 * | 7/2010 | Ohta | A61B 6/4233 250/370.09 |
| 8,010,177 | B2 * | 8/2011 | Csavoy | A61B 34/20 600/407 |
| 8,019,041 | B2 * | 9/2011 | Tomisaki | A61B 5/0031 378/51 |
| 8,045,677 | B2 * | 10/2011 | Movassaghi | A61B 6/04 378/196 |
| 8,118,488 | B2 * | 2/2012 | Gregerson | A61B 5/0555 378/198 |
| 8,165,658 | B2 * | 4/2012 | Waynik | A61B 34/20 600/407 |
| 8,177,430 | B2 * | 5/2012 | Bouvier | A61B 6/4405 378/198 |
| 8,242,925 | B2 * | 8/2012 | Graumann | A61B 34/20 340/686.2 |
| 8,325,873 | B2 * | 12/2012 | Helm | A61B 6/02 378/15 |
| 8,351,574 | B2 * | 1/2013 | Takemoto | A61B 5/02007 378/4 |
| 8,358,740 | B2 * | 1/2013 | Nakatsugawa | A61B 6/102 378/116 |
| 8,363,786 | B2 * | 1/2013 | Nakatsugawa | A61B 6/4441 378/116 |
| 8,374,678 | B2 * | 2/2013 | Graumann | A61B 6/12 378/205 |
| 8,408,788 | B2 * | 4/2013 | Ozawa | A61B 6/102 378/197 |
| 8,475,041 | B2 * | 7/2013 | Takemoto | A61B 6/548 378/197 |
| 8,532,262 | B2 * | 9/2013 | Iwakiri | A61B 6/4233 250/370.09 |
| 8,562,211 | B2 * | 10/2013 | Helm | A61B 6/035 378/194 |
| 8,591,107 | B2 * | 11/2013 | Peters | A61B 6/4441 378/193 |
| 8,708,561 | B2 * | 4/2014 | Eaves | A61B 6/4233 378/198 |
| 8,721,179 | B2 * | 5/2014 | Watanabe | A61B 5/0555 378/209 |
| 8,737,567 | B2 * | 5/2014 | Shah | A61B 6/405 378/95 |
| 8,768,029 | B2 * | 7/2014 | Helm | A61B 6/4476 382/131 |
| 8,794,832 | B2 * | 8/2014 | Noda | A61B 6/4441 378/193 |
| 8,798,236 | B2 * | 8/2014 | Ohta | A61B 6/4494 250/370.09 |
| 8,804,908 | B2 * | 8/2014 | Hibino | A61B 6/4405 378/98 |
| 8,882,348 | B2 * | 11/2014 | Herrmann | A61B 6/4441 378/198 |
| 8,886,286 | B2 * | 11/2014 | Graumann | A61B 6/12 600/414 |
| 8,899,834 | B2 * | 12/2014 | Barker | A61B 6/4405 250/370.09 |
| 8,929,510 | B2 * | 1/2015 | Nishino | A61B 6/4216 378/102 |
| 8,971,495 | B2 * | 3/2015 | Shah | A61B 6/032 378/101 |
| 8,983,663 | B2 * | 3/2015 | Marar | A61B 5/055 700/246 |
| 9,020,097 | B2 * | 4/2015 | Iwakiri | A61B 6/4283 378/42 |
| 9,084,582 | B2 * | 7/2015 | Omura | A61B 6/4405 |
| 9,125,611 | B2 * | 9/2015 | Eaves | A61B 6/4405 |
| 9,173,628 | B2 * | 11/2015 | Bouvier | A61B 6/4405 |
| 9,192,343 | B2 * | 11/2015 | Eklund | A61B 6/06 |
| 9,259,203 | B2 * | 2/2016 | Bouvier | A61B 6/4405 |
| 9,265,470 | B2 * | 2/2016 | Simmons | A61B 6/447 |
| 9,295,438 | B2 * | 3/2016 | Omura | A61B 6/4405 |
| 9,345,440 | B2 * | 5/2016 | Graumann | A61B 6/547 |
| 9,398,885 | B2 * | 7/2016 | Suzuki | A61B 6/42 |
| 9,492,131 | B2 * | 11/2016 | Meek | A61B 6/4476 |
| 9,613,438 | B2 * | 4/2017 | Takemoto | G06T 11/005 |
| 9,642,584 | B2 * | 5/2017 | Niebler | A61B 6/4441 |
| 9,687,200 | B2 * | 6/2017 | Maurer, Jr. | A61B 6/032 |
| 9,693,437 | B2 * | 6/2017 | Simmons | G01N 23/04 |
| 9,693,740 | B2 * | 7/2017 | Hori | A61B 6/0457 |
| 9,693,746 | B2 * | 7/2017 | Ancar | A61B 6/08 |
| 9,737,235 | B2 * | 8/2017 | Hartmann | A61B 5/06 |
| 9,782,143 | B2 * | 10/2017 | Graumann | A61B 6/54 |
| 9,795,357 | B2 * | 10/2017 | Carelsen | A61B 6/547 |
| 9,833,209 | B2 * | 12/2017 | Belei | A61B 6/4441 |
| 9,883,841 | B2 * | 2/2018 | Baat | A61B 6/4405 |

(56) References Cited

U.S. PATENT DOCUMENTS

| | | | |
|---|---|---|---|
| 9,895,118 B2* | 2/2018 | Zaiki | A61B 6/469 |
| 9,955,927 B2* | 5/2018 | Hendriks | A61B 6/025 |
| 9,968,320 B2* | 5/2018 | Zaiki | A61B 6/467 |
| 9,986,962 B2* | 6/2018 | Imagawa | A61B 6/022 |
| 10,028,788 B2* | 7/2018 | Kang | A61B 6/4441 |
| 10,076,293 B2* | 9/2018 | Sehnert | A61B 6/06 |
| 10,136,864 B2* | 11/2018 | Maack | A61B 6/06 |
| 10,213,171 B2* | 2/2019 | Masuo | A61B 6/08 |
| 10,226,222 B2* | 3/2019 | Sakata | A61B 6/0407 |
| 10,517,548 B2* | 12/2019 | Kojima | A61B 6/102 |
| 2008/0119714 A1 | 5/2008 | Meissner et al. | |
| 2010/0299014 A1 | 11/2010 | Bouvier | |

FOREIGN PATENT DOCUMENTS

| | | |
|---|---|---|
| JP | 2011-229900 | 11/2011 |
| JP | 2013-512065 | 4/2013 |
| JP | 2013-514138 | 4/2013 |

OTHER PUBLICATIONS

Written Opinion dated Jun. 24, 2014 in PCT/JP2014/064634 filed Jun. 2, 2014.

* cited by examiner

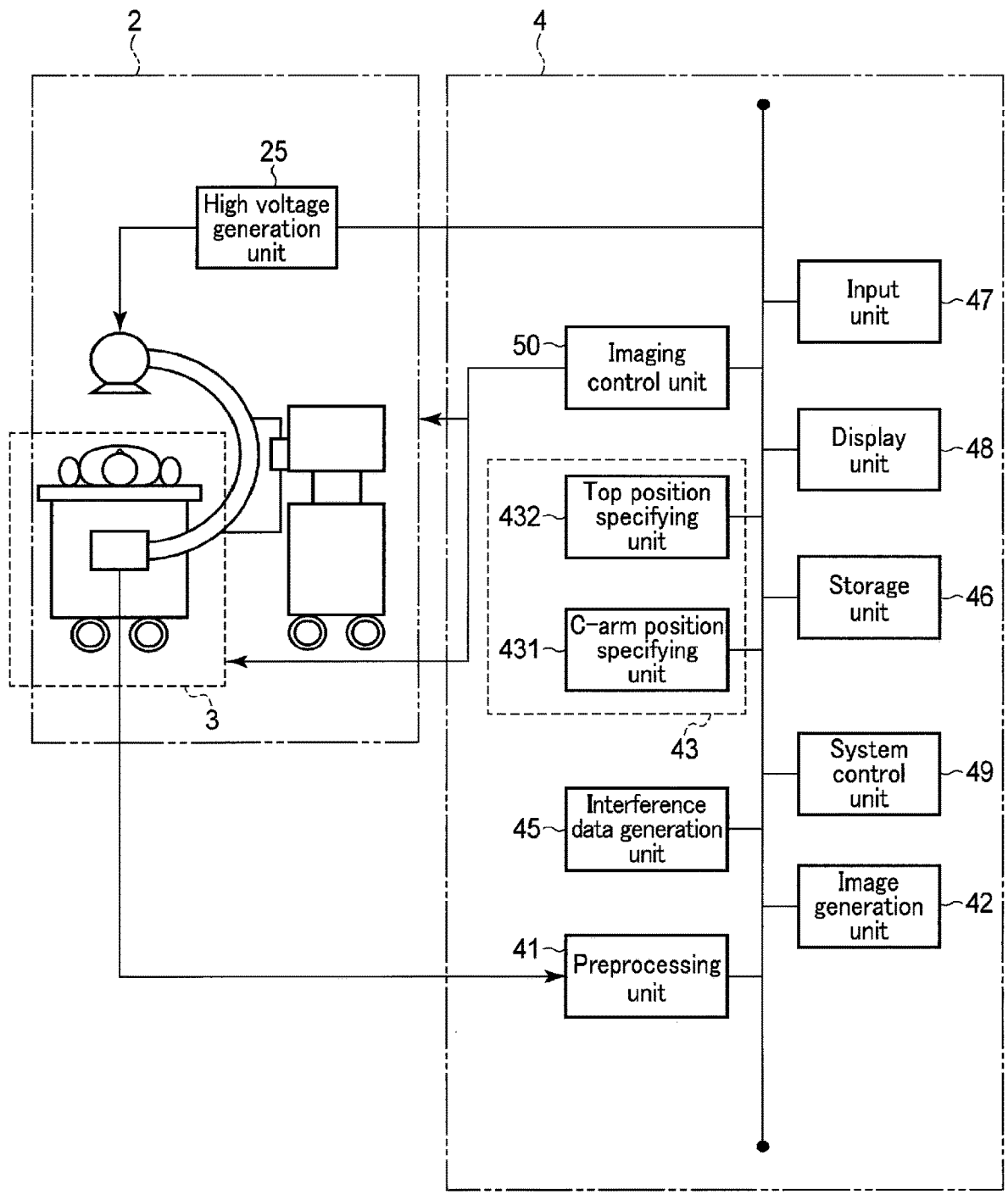
F I G. 1

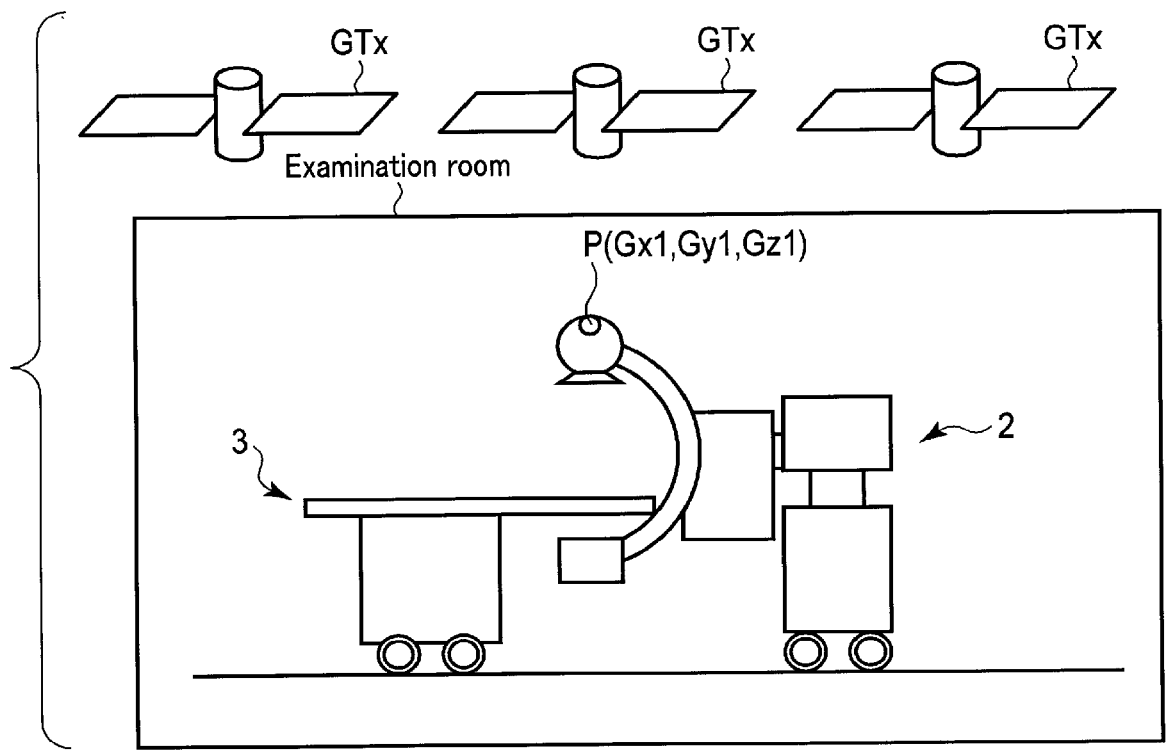
F I G. 5
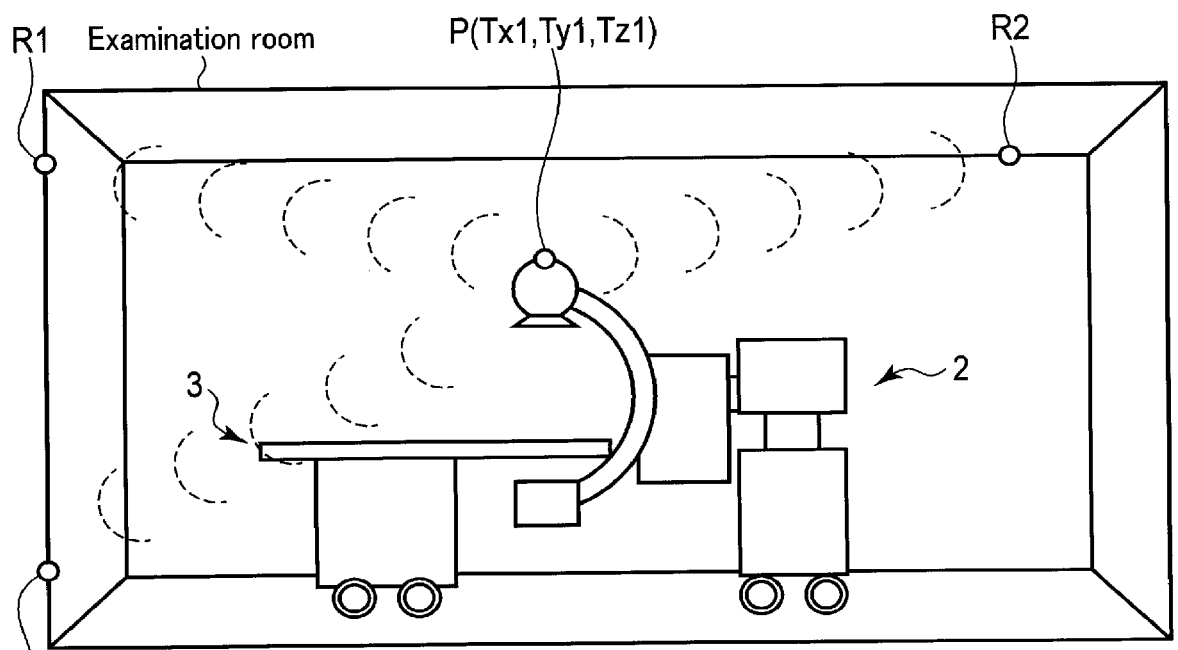
F I G. 6

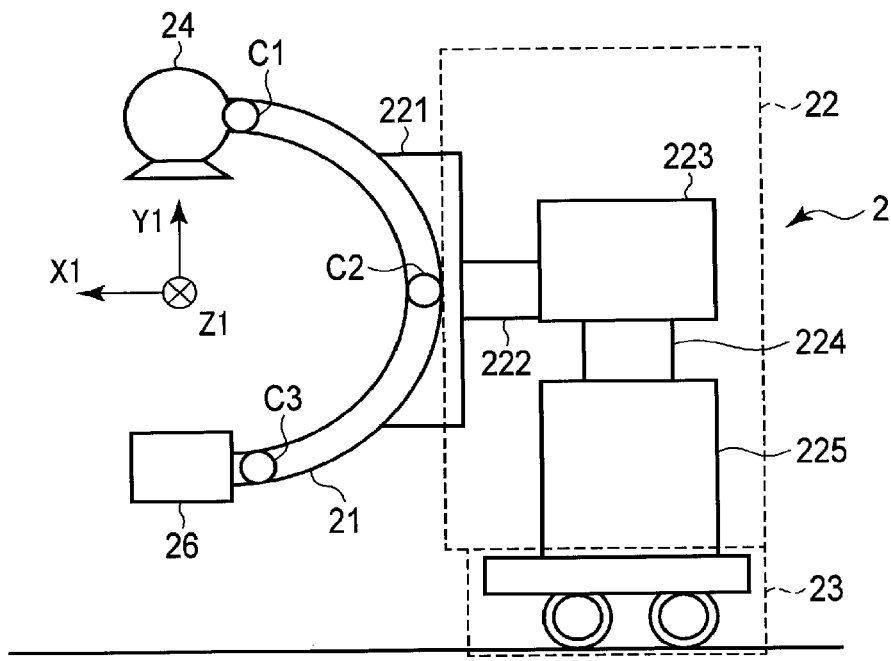
F I G. 7A
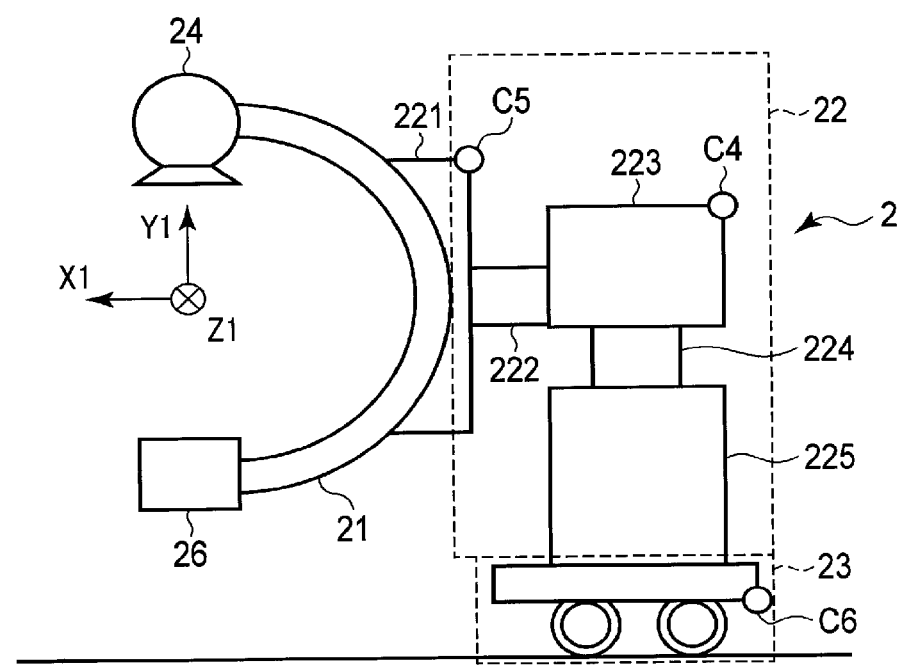
F I G. 7B

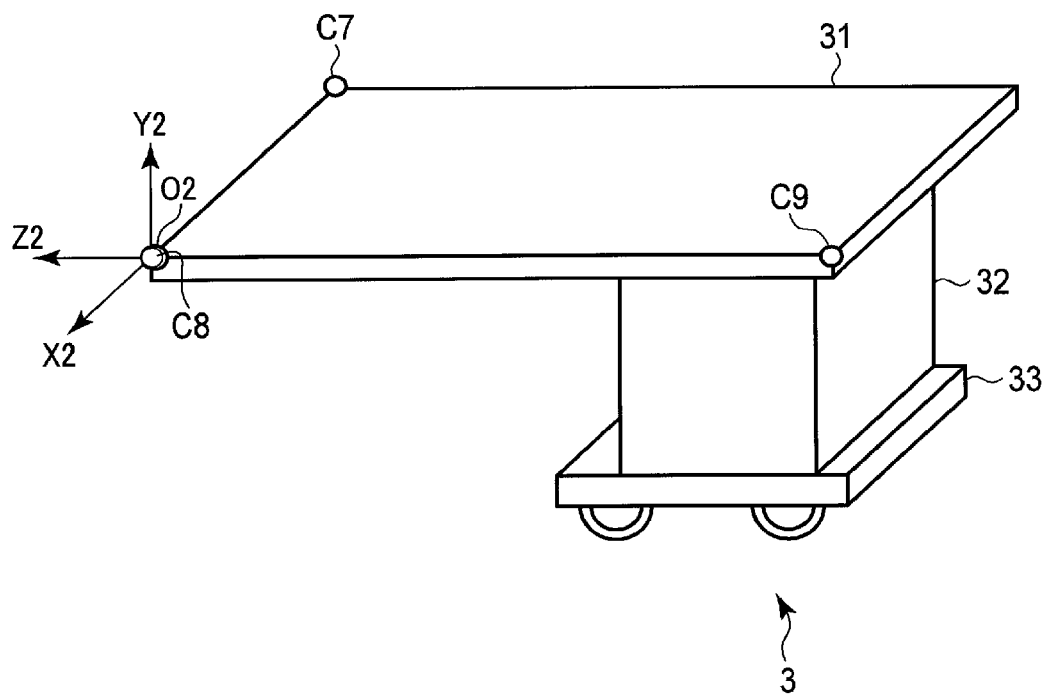
F I G. 8

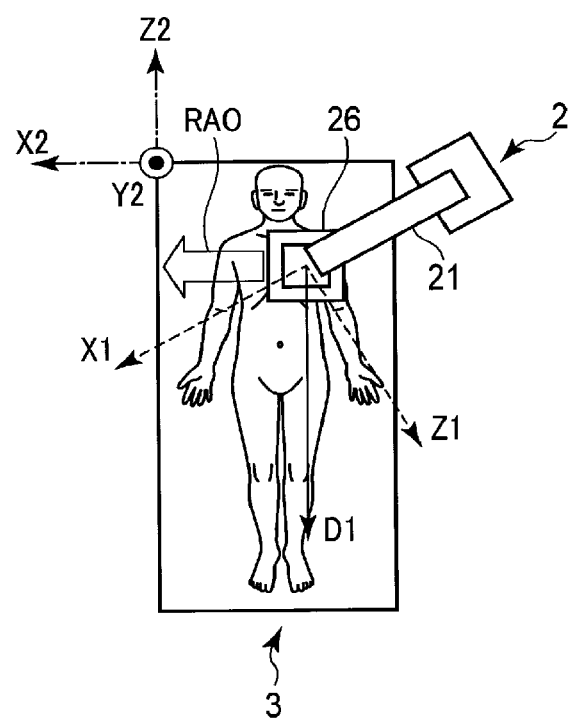
F I G. 13C

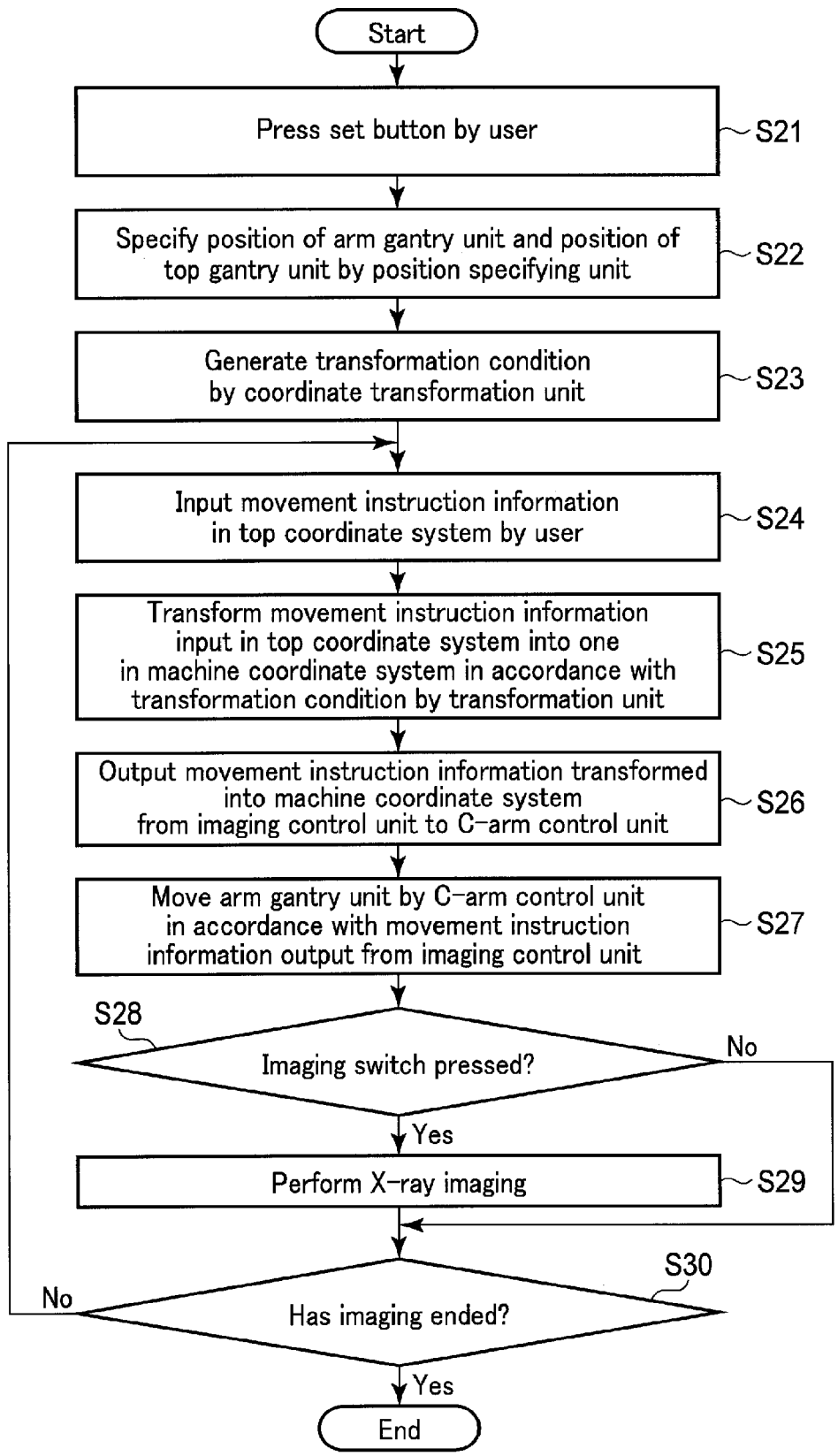
F I G. 14

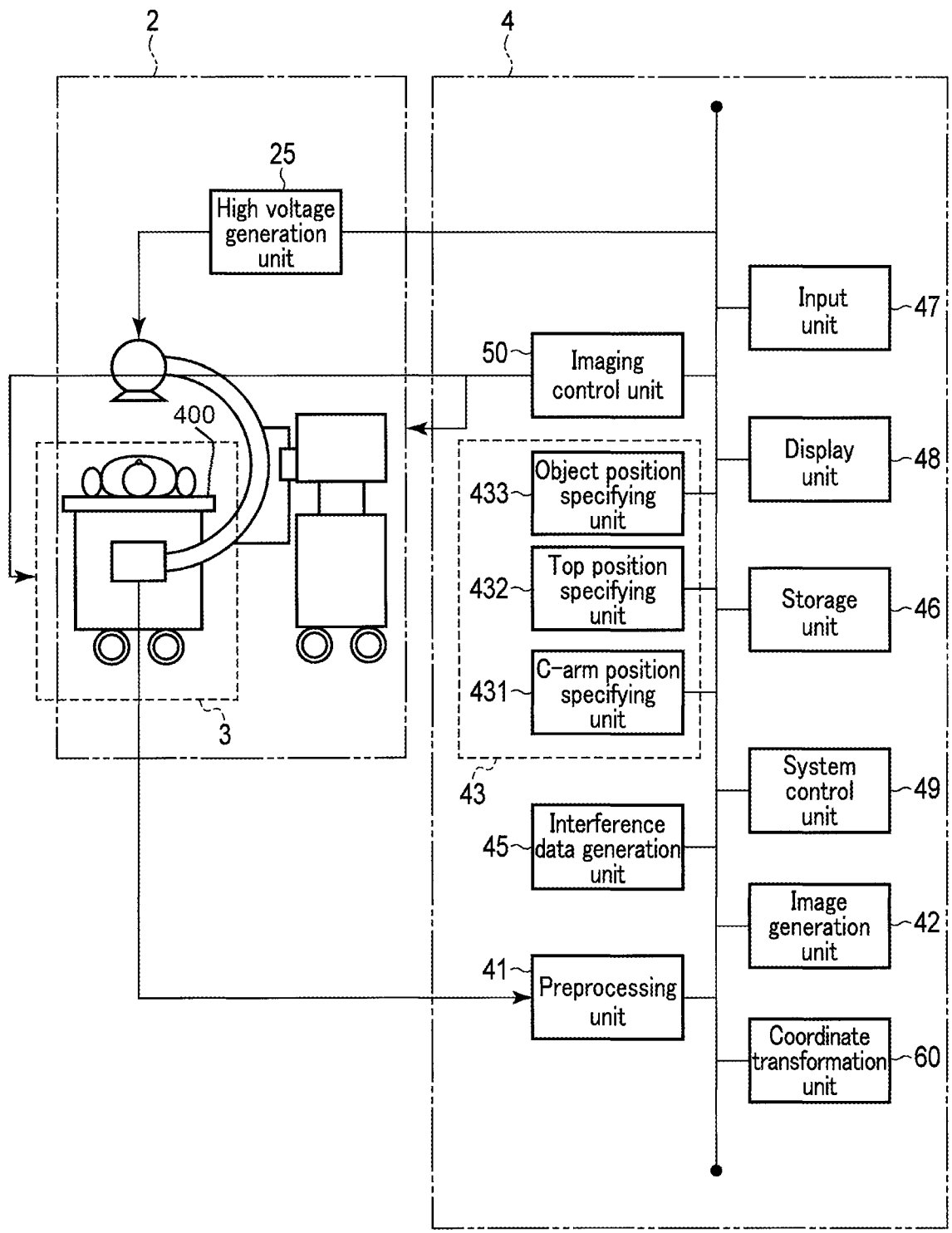
F I G. 15

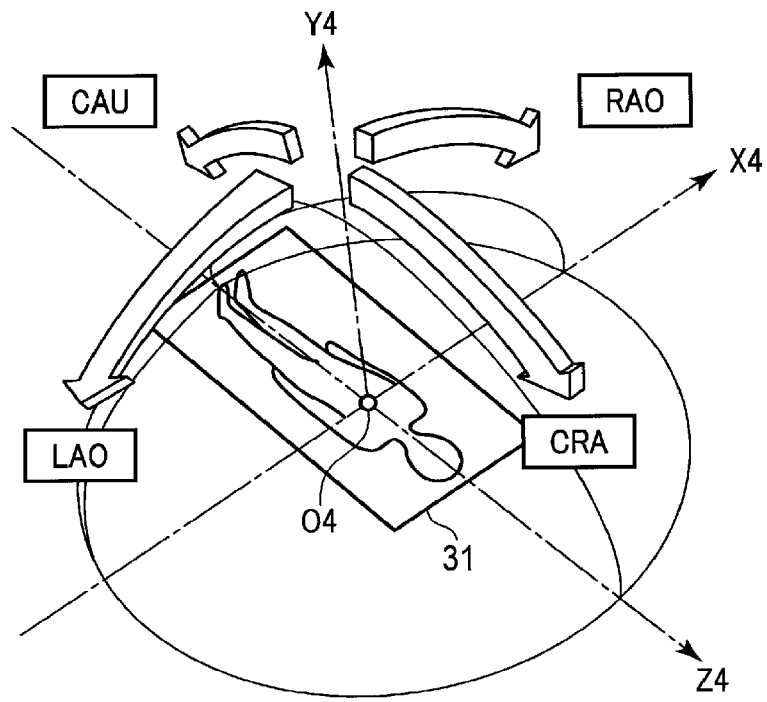
F I G. 16
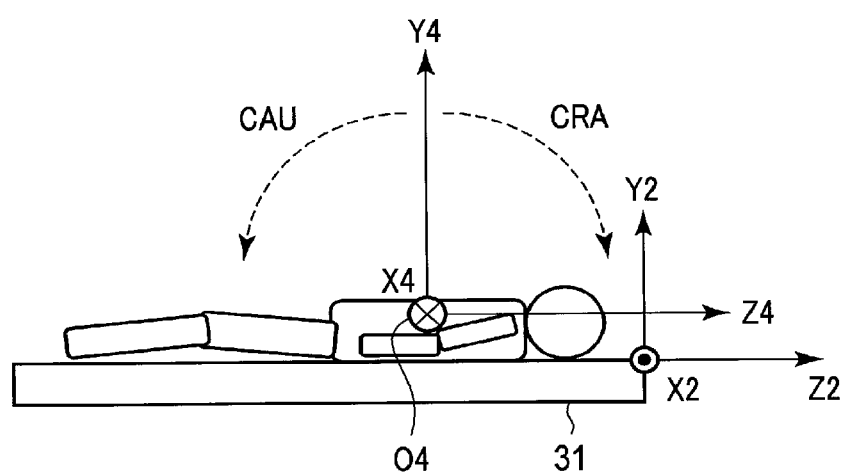
F I G. 17A

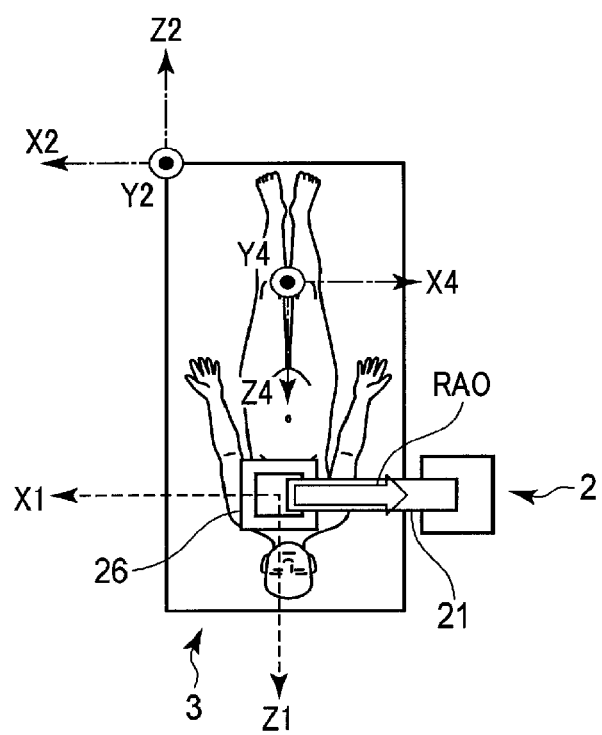
F I G. 18B

X-RAY DIAGNOSTIC APPARATUS COMPRISING A POSITION SPECIFYING UNIT AND A CONTROL UNIT

This application is a Continuation Application of PCT Application No. PCT/JP2014/064634, filed Jun. 2, 2014 and based upon and claims the benefit of priority from the Japanese Patent Application No. 2013-115579, filed May 31, 2013, the entire contents of all of which are incorporated herein by reference.

FIELD

Embodiments described herein relate generally to an X-ray diagnostic apparatus.

BACKGROUND

A radiation medical image diagnostic apparatus such as an X-ray diagnostic apparatus is an apparatus which provides medical information of an object based by an image based on the intensity of X-rays having passed through the object. The radiation medical image diagnostic apparatus plays an important role in medical practice including diagnosis and treatment. When imaging an object using an X-ray diagnostic apparatus, the object needs to be imaged from various angles in order to obtain effective information from the object. To do this, for example, the X-ray diagnostic apparatus has an auto-positioning function of registering in advance the position and angle of a C-arm which holds an X-ray tube and an X-ray detector, and moving the C-arm and a top to the registered positions by a simple input operation (input from a preset button).

However, to execute the auto-positioning function, the position of the C-arm and that of the top need to be associated with each other. For example, in a system in which a portable C-arm or top having wheels is combined, the position of the top and that of the C-arm are not associated with each other, so the above-mentioned auto-positioning function cannot be executed. The user needs to move the C-arm and the top by a manual operation, and a long time is taken to move the C-arm and the top.

SUMMARY OF INVENTION

Technical Problem

An object is to easily align an object with respect to an imaging position in an X-ray diagnostic apparatus including at least a portable C-arm or a portable top.

Solution to Problem

BRIEF DESCRIPTION OF THE DRAWINGS

FIG. 1 is a block diagram showing the arrangement of an X-ray diagnostic apparatus according to the first embodiment.

FIG. 5 is an explanatory view for explaining a method of specifying the position of the arm gantry by a C-arm position specifying unit when a GPS is used.

FIG. 6 is an explanatory view for explaining a method of specifying the position of the arm gantry by the C-arm position specifying unit when an ultrasonic system is used.

FIG. 7A is a view showing the first example of a plurality of positions on the arm gantry of the X-ray diagnostic apparatus according to the first embodiment.

FIG. 7B is a view showing the second example of a plurality of positions on the arm gantry of the X-ray diagnostic apparatus according to the first embodiment.

FIG. 8 is a view showing an example of a plurality of positions on the top gantry of the X-ray diagnostic apparatus according to the first embodiment.

FIG. 13C is a view schematically showing a state in which the C-arm is inserted from a direction oblique to the long- and short-axis directions of the top.

FIG. 14 is a flowchart showing a series of workflow operations when the X-ray diagnostic apparatus according to the second embodiment is used.

FIG. 15 is a block diagram showing the arrangement of an X-ray diagnostic apparatus according to the third embodiment.

FIG. 16 is a view showing a clinical coordinate system.

FIG. 17A is a view showing the first example of the positional relationship between the clinical coordinate system and the top coordinate system.

FIG. 18B is a view schematically showing a state in which the position of the patient in FIG. 18A is turned upside down with respect to the top.

DESCRIPTION OF EMBODIMENTS

Detailed Description

Figure 2:
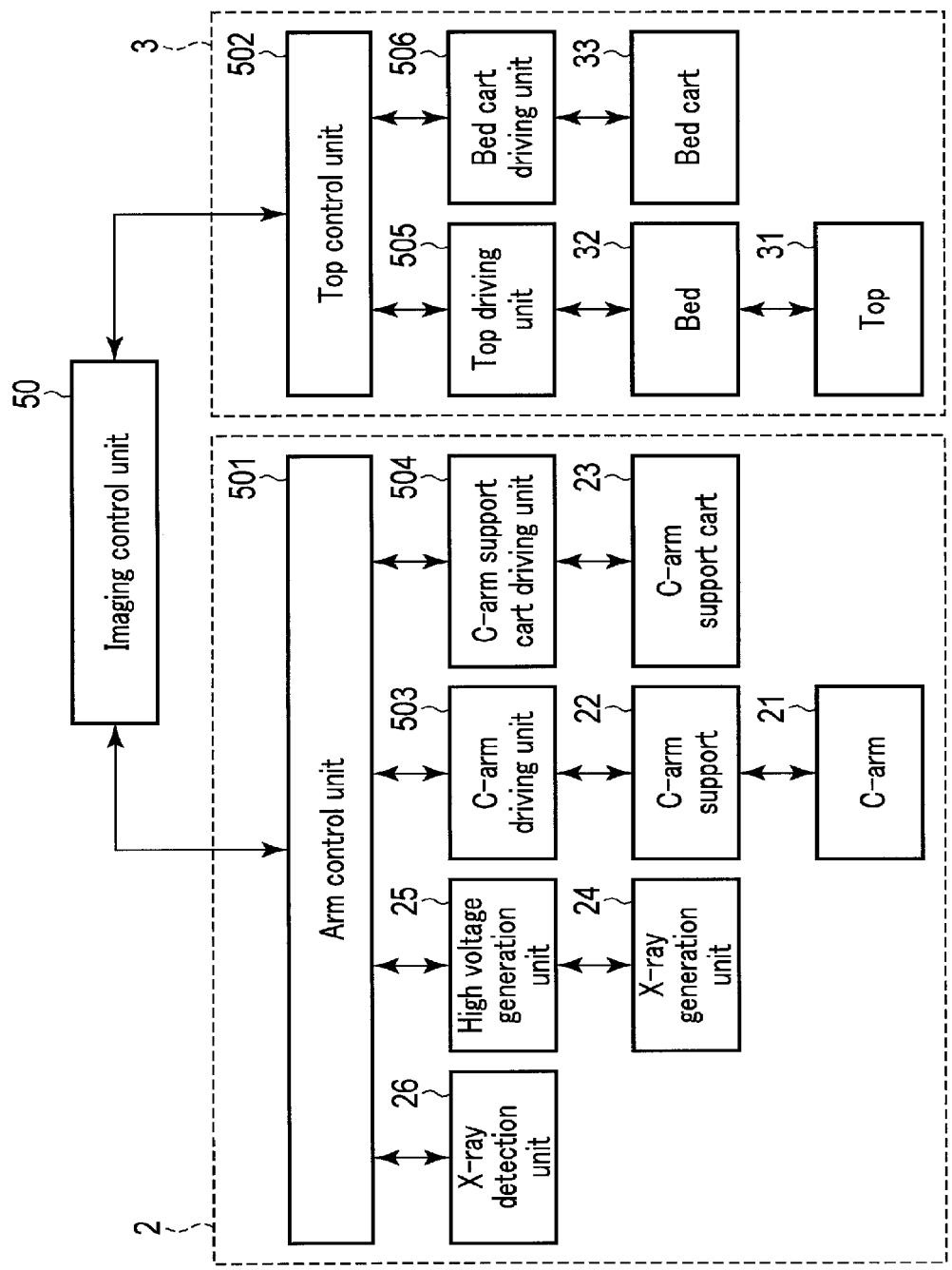
FIG. 2 is a block diagram showing the arrangements of an arm gantry and top gantry.

An X-ray diagnostic apparatus according to one embodiment comprises an X-ray tube, an X-ray detector, a holding mechanism, position specifying circuitry and control circuitry. The X-ray detector detects the X-ray which has been generated by the X-ray tube and has passed through an object placed on a top of a bed movable in an examination room. The holding mechanism holds the X-ray tube and the X-ray detector, and movable in the examination room. The position specifying circuitry specifies a position of the holding mechanism in the examination room and a position of the bed in the examination room. The control circuitry controls the holding mechanism in order to change a position and angle of the holding mechanism based on the position of the holding mechanism and the position of the bed.

X-ray diagnostic apparatuses according to the first, second, third, and fourth embodiments will now be described with reference to the accompanying drawings. Note that the same reference numerals denote constituent elements having almost the same functions and arrangements in the following description, and a repetitive description will be made only when required.

First Embodiment

FIG. 1 is a block diagram showing the arrangement of an X-ray diagnostic apparatus according to the first embodiment. The X-ray diagnostic apparatus according to the first embodiment includes an arm gantry 2, a top gantry 3, and a data processing device 4. Note that the first, second, and third embodiments for practicing the present invention will explain an X-ray diagnostic apparatus constituted by a portable arm gantry 2 and a portable top gantry 3. The portable arm gantry 2 and the top gantry 3 can be freely moved for every gantry in an examination room. That is, neither part of the arm gantry 2 nor part of the top gantry 3 is fixed in the examination room. However, the embodiment is applicable to even an X-ray diagnostic apparatus in which at least one of the arm gantry 2 and top gantry 3 has portability.

Next, the arrangements of the arm gantry 2 and top gantry 3 of the X-ray diagnostic apparatus according to the first embodiment will be explained with reference to FIGS. 2, 3A, and 3B.

FIG. 2 is a block diagram showing the arrangements of the arm gantry 2 and top gantry 3. As already described above, the arm gantry 2, the top gantry 3, and the data processing device 4 are independent devices. Each of the arm gantry 2 and top gantry 3 performs an operation complying with a control signal from the data processing device 4. The data processing device 4 includes an imaging control unit 50. The arm gantry 2 includes an arm control unit 501. The top gantry 3 includes a top control unit 502. Each of the imaging control unit 50, arm control unit 501, and top control unit 502 includes a wireless communication unit (not shown), and can communicate data with another apparatus via a network such as a LAN (Local Area Network) or a public electronic communication line. The following description assumes that the arm control unit 501 and the top control unit 502 perform respective control operations in accordance with control signals from the imaging control unit 50.

The arm control unit 501 controls each unit of the arm gantry 2 based on a control signal output from the imaging control unit 50. For example, the arm control unit 501 controls a high voltage generation unit 25, an X-ray detection unit 26, a C-arm driving unit 503, and a C-arm support cart driving unit 504 so as to synchronize movement of a C-arm 21, generation of X-rays, and detection of X-rays in order to execute X-ray imaging in accordance with X-ray imaging conditions. More specifically, the arm control unit 501 controls the high voltage generation unit 25 in accordance with a tube current, tube voltage, irradiation time, and the like included in the X-ray imaging conditions. At this time, the arm control unit 501 controls the X-ray detection unit 26 in synchronism with the control of the high voltage generation unit. The arm control unit 501 outputs, to the imaging control unit 50, an electrical signal output from the X-ray detection unit 26. The arm control unit 501 controls the C-arm driving unit 503 and the C-arm support cart driving unit 504 based on a movement control signal output from the imaging control unit 50. The arm gantry 2 is moved by driving the C-arm driving unit 503 and the C-arm support cart driving unit 504. Note that this movement includes rotational movement and translational movement. The operation of the arm gantry 2 will be explained with reference to FIG. 3A. The operation of the top gantry 3 will be explained with reference to FIG. 3B.

Figure 3A:
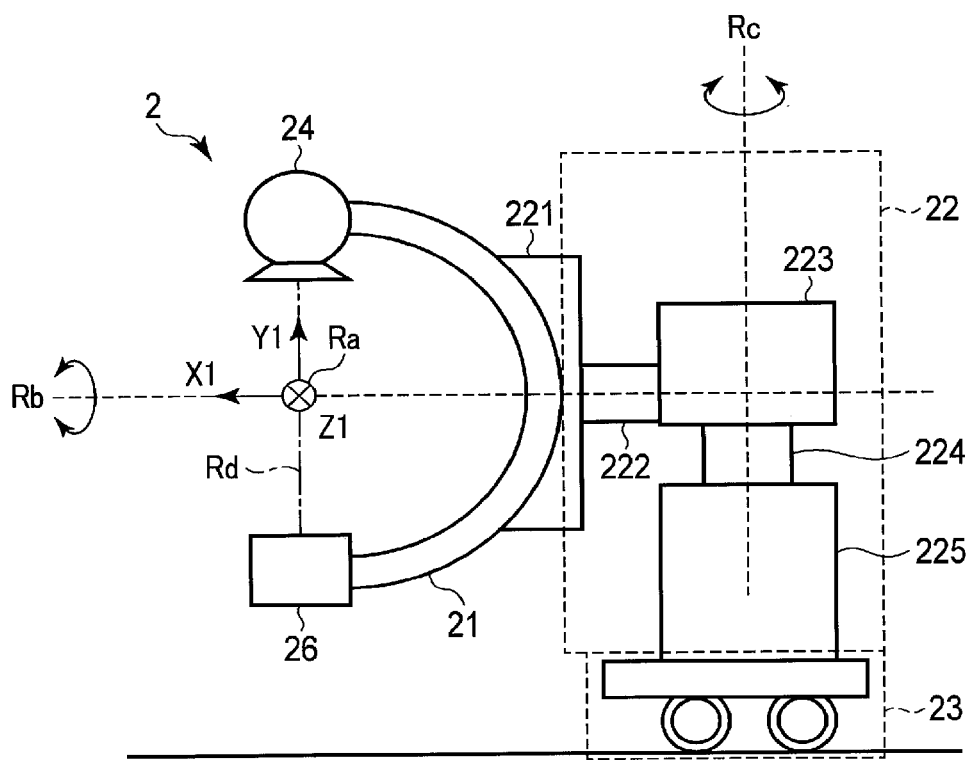
FIG. 3A is a view showing an example of the outer appearance of the arm gantry of the X-ray diagnostic apparatus according to the first embodiment.

FIG. 3A is a view showing an example of the outer appearance of the arm gantry 2 of the X-ray diagnostic apparatus according to the first embodiment. The arm gantry 2 includes the C-arm 21, a C-arm support 22, a C-arm support cart 23, an X-ray generation unit 24, the high voltage generation unit 25 (not shown), and the X-ray detection unit 26. The C-arm support 22 movably supports the C-arm 21. The C-arm support 22 includes a C-arm holder 221, a first moving mechanism 222, a first support 223, a second moving mechanism 224, and a second support 225. Note that each of mechanisms which support the X-ray generation unit 24 and the X-ray detection unit 26, for example, each of the C-arm support 22 and the C-arm support cart 23 will also be called a holding unit.

The C-arm 21 has a plurality of rotation axes. The C-arm 21 can rotate about the plurality of rotation axes by driving the C-arm driving unit 503.

The C-arm driving unit 503 includes a slide moving mechanism driving unit, a first moving mechanism driving unit, a second moving mechanism driving unit, and a third moving mechanism driving unit (none are shown). The C-arm holder 221 supports the C-arm 21 via a slide moving mechanism. The slide moving mechanism slides and rotates the C-arm 21 in an arc shape along the shape of the C-arm 21 by driving the slide moving mechanism driving unit. A rotation axis Ra of this slide rotation is an axis parallel to the floor surface.

The first support 223 supports the C-arm holder 221 via the first moving mechanism 222. By driving the first moving mechanism driving unit, the first moving mechanism 222 is rotated about a rotation axis Rb which is parallel to the floor surface and perpendicular to the slide rotation axis Ra. Accordingly, the C-arm 21 can rotate about the rotation axis Rb.

The second support 225 supports the first support 223 via the second moving mechanism 224. By driving the second moving mechanism driving unit, the second moving mechanism 224 is rotated about a rotation axis Rc perpendicular to the floor surface. The C-arm 21 can therefore rotate about the rotation axis Rc. By driving the third moving mechanism driving unit, the second moving mechanism 224 vertically moves the first support 223 in a direction perpendicular to the floor surface. An imaging axis Rd is an axis connecting the X-ray focus of the X-ray generation unit 24 and the center position of the X-ray detection surface of the X-ray detection unit 26. The rotation axis Ra, the rotation axis Rb, and the imaging axis Rd cross each other at the isocenter.

The C-arm support cart 23 supports the C-arm support 22 movably in a direction parallel to the floor surface. The C-arm support cart 23 has wheels for moving on the floor surface. The C-arm support cart 23 is moved by driving the C-arm support cart driving unit 504 and rotating the wheels. The C-arm 21 is moved together with the C-arm support cart 23. Note that the C-arm support 22 may include another moving mechanism in addition to the above-described moving mechanisms. For example, the first moving mechanism 222 may include a moving mechanism that performs an expansion/contraction operation. The C-arm 21 can therefore be moved in one direction parallel to the floor surface.

In short, the C-arm 21 can tilt the imaging axis Rd to all angles with respect to the isocenter by a rotational operation about the rotation axes Ra and Rb. The C-arm 21 can be translated in the three axial directions by movement of the C-arm support cart 23, the elevation operation of the second moving mechanism 224, and the like.

The arm control unit 501 controls each driving unit in accordance with a translation amount, translation direction, rotation angle, and rotation direction included in a movement control signal received from the imaging control unit 50. The moving amount and the moving direction are represented by the coordinate system of the arm gantry 2. The coordinate system of the arm gantry 2 will be called a machine coordinate system. To simplify the description, the origin of the machine coordinate system is the isocenter in the initial state of the arm gantry 2, the X-axis is an axis X1 parallel to the rotation axis Rb, the Z-axis is an axis Z1 parallel to the rotation axis Ra, and the Y-axis is an axis Y1 perpendicular to the X-axis X1 and the Z-axis Z1. The initial state of the arm gantry 2 is a state in which each mechanism is returned to its reference position.

For example, when the movement control signal includes a signal designating "move by 50 mm in the X1 direction", the arm control unit 501 controls the C-arm support cart driving unit 504 to move the C-arm support cart 23 by 50 mm in the X1 direction together with the C-arm 21. When the movement control signal includes a signal designating "rotate by +20° about the slide rotation axis Ra", the arm control unit 501 controls the slide moving mechanism driving unit to rotate the slide moving mechanism by +20° together with the C-arm 21.

Figure 3B:
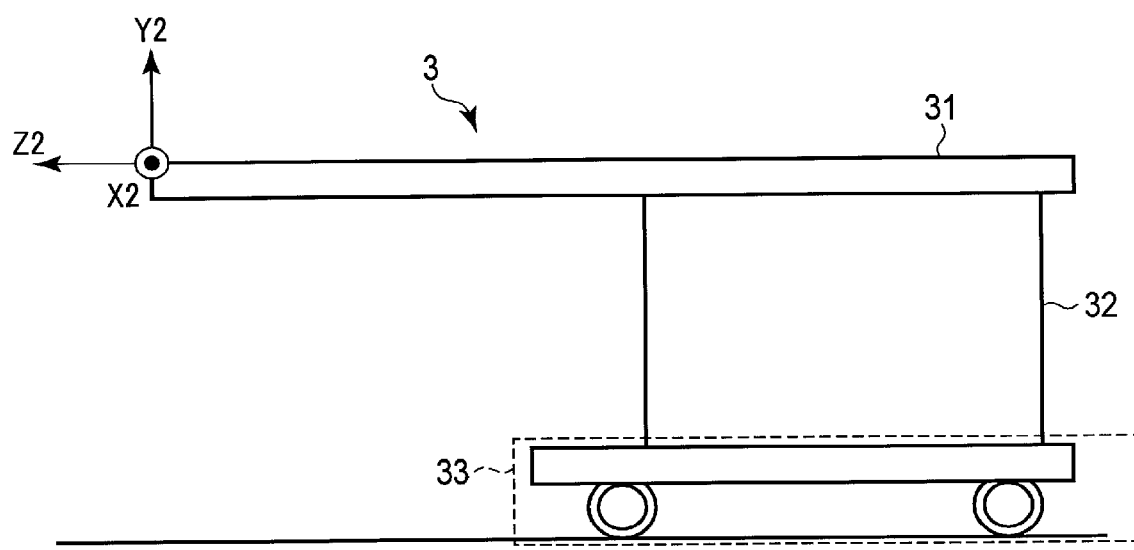
FIG. 3B is a view showing an example of the outer appearance of the top gantry of the X-ray diagnostic apparatus according to the first embodiment.

FIG. 3B is a view showing an example of the outer appearance of the top gantry 3 of the X-ray diagnostic apparatus according to the first embodiment. The top gantry 3 includes a top 31, a bed 32, and a bed cart 33. The bed 32 movably supports the top 31. The top 31 is moved by driving a top driving unit 505. For example, the top 31 is vertically moved in a direction perpendicular to the floor surface. The top 31 is translated on a plane parallel to the floor surface. Note that the top 31 is tilted with reference to the long and minor axes of the top. The bed cart 33 supports the bed 32 so that the bed 32 can be translated on a plane parallel to the floor surface. The bed cart 33 has wheels for moving on the floor surface. The bed cart 33 moves the bed 32 together with the top 31 by driving a bed cart driving unit 506 and rotating the wheels.

The top control unit 502 controls each driving unit in accordance with a translation amount and translation direction included in a movement control signal received from the imaging control unit 50. The moving amount and the moving direction are represented by the coordinate system of the top gantry 3. The coordinate system of the top gantry 3 will be called a top coordinate system. The X-axis of the top coordinate system is an axis X2 parallel to the short axis of the top 31, the Y-axis is an axis Y2 perpendicular to the surface of the top 31 (or the floor surface), and the Z-axis is an axis Z2 parallel to the long axis of the top 31. The origin of the top coordinate system is set at a predetermined position in the initial state of the top gantry 3. For example, the origin of the top coordinate system is set at one corner of the top 31 when the top 31 is returned to its reference position.

For example, when the movement control signal includes a signal designating "move by 30 mm in the X2 direction", the top control unit 502 controls the top driving unit 505 to move the top 31 by 30 mm in the X2 direction. Note that the top control unit 502 may control the bed cart driving unit 506 to move the top 31 by 30 mm in the X2 direction together with the bed 32. When the movement control signal includes a driving target, the top control unit 502 controls the driving target. For example, when the movement control signal includes a signal designating "control the top driving unit 505 to move the top 31 by 30 mm in the Z2 direction", the top control unit 502 controls the top driving unit 505 to move the top 31 by 30 mm in the Z2 direction.

The C-arm 21 holds the X-ray generation unit 24 at one end. The X-ray generation unit 24 includes an X-ray tube, an X-ray filter, and an X-ray stop. The X-ray tube receives application of a high voltage (tube voltage) and supply of a tube current from the high voltage generation unit 25, and generates X-rays from the focus. The X-ray filter changes the radiation quality of X-rays, and removes long-wavelength components unnecessary for diagnosis from the continuous spectrum of X-rays generated from the focus, for the purpose of reduction of the X-ray exposure of an object, improvement of the image quality, and the like. The X-ray stop includes a plurality of independently controllable aperture blades for limiting an X-ray irradiation range on the detection surface of the X-ray detection unit 26 for X-rays which have been radiated from the focus and have passed through the X-ray filter. The plurality of aperture blades are independently moved under the control of a system control unit 49.

The C-arm 21 holds the X-ray detection unit 26 at the other end so that the X-ray detection unit 26 faces the X-ray generation unit 24. The X-ray detection unit 26 includes a plurality of X-ray detection elements. The plurality of X-ray detection elements are two-dimensionally arrayed. A detector of the two-dimensional array shape is called an FPD (Flat Panel Display). Each element of the FPD detects X-rays which have been radiated from the X-ray generation unit 24 and have passed through an object. Each element of the FPD outputs an electrical signal corresponding to a detected X-ray intensity. Although the C-arm 21 is described as a mechanism which holds the X-ray generation unit 24 and the X-ray detection unit 26, the holding mechanism is not limited to the C-arm 21 as long as the mechanism can hold the X-ray generation unit 24 and the X-ray detection unit 26. For example, the C-arm 21 can be replaced with an Ω-arm.

The data processing device 4 includes a preprocessing unit 41, an image generation unit 42, a position specifying unit 43, an interference data generation unit 45, a storage unit 46, an input unit 47, a display unit 48, the system control unit 49, and the imaging control unit 50.

The preprocessing unit 41 executes preprocessing on an electrical signal output from the X-ray detection unit 26. The preprocessing includes various types of correction processing, amplification processing, and A/D conversion processing.

The image generation unit 42 generates X-ray image data based on the electrical signal having undergone preprocessing. A pixel value assigned to each pixel constituting an X-ray image is, e.g., a value corresponding to an X-ray attenuation coefficient concerning a substance on the transmission path of X-rays.

The input unit 47 functions as an interface for inputting instruction information by the user to the X-ray diagnostic apparatus according to the first embodiment. The instruction information includes movement instructions for the arm gantry 2 and the top gantry 3, a preset registration instruction, an auto-positioning function execution instruction, and a control priority setting instruction. The input unit 47 includes an operation console for moving each of the arm gantry 2 and top gantry 3 to a position desired by the user. The operation console includes buttons, a handle, a track ball, and the like. The operation console is common to the arm gantry 2 and the top gantry 3. Note that the operation console may include an operation console dedicated to the arm gantry 2 and an operation console dedicated to the top gantry 3. The user can freely move the arm gantry 2 and the top gantry 3 by operating the operation console.

The operation console includes a plurality of preset buttons corresponding to the auto-positioning function. Each preset button is a button that triggers execution of the auto-positioning function by the X-ray diagnostic apparatus. The auto-positioning function is a function of automatically performing alignment between the arm gantry 2 and the top gantry 3. Since the auto-positioning function can reduce the labor to manually perform alignment, a series of workflow operations concerning imaging can be improved. Note that this alignment is alignment of the imaging axis with respect to the top 31. Hence, each of the arm gantry 2 and top gantry 3 can be automatically arranged at a desired imaging position. Note that the alignment may be alignment between a plurality of mechanisms constituting the arm gantry 2 and a plurality of mechanisms constituting the top gantry 3. In this case, alignment between the C-arm support cart 23 and the bed cart 33 is also performed. The embodiment will be explained below by exemplifying a case in which alignment of the imaging axis with respect to the top 31 is performed with a higher degree of freedom of the arrangement of each of the arm gantry 2 and top gantry 3.

The plurality of preset buttons correspond to respective relative positions. The relative position concerns the position of the imaging axis with respect to the top 31. By only pressing the preset button, the user can align the imaging axis with respect to the top 31.

Control priority indicates the priority order of a mechanism to be moved at the time of executing the auto-positioning function. For example, when the user does not want to positively move the top gantry 3, he sets control priority "high" for the arm gantry 2 and control priority "low" for the top gantry 3. Although control priority between the arm gantry 2 and the top gantry 3 is described here, the user can set control priority for each of a plurality of driving units constituting each of the arm gantry 2 and top gantry 3.

The storage unit 46 is a semiconductor storage device such as a flash SSD (Solid State Disk) serving as a semiconductor storage element, an HDD (Hard Disk Drive), or the like. The storage unit 46 stores data of an X-ray image generated by the image generation unit 42, and the like. Also, the storage unit 46 stores interference data which is generated by the interference data generation unit 45 (to be described later) and concerns the mechanical positional relationship between the arm gantry 2 and the top gantry 3. Further, the storage unit 46 stores data of a plurality of relative positions corresponding to the respective preset buttons. Data of relative positions are data representing the position and direction of the imaging axis with respect to the top 31. For example, to obtain the position and direction of the imaging axis with respect to the top 31, it is only necessary to obtain the position of the X-ray generation unit 24 and that of the X-ray detection unit 26 with respect to a predetermined position of the top 31. If the positional relationship between the position of the X-ray generation unit 24, the position of the X-ray detection unit 26, and the imaging axis is registered in advance, the position and direction of the imaging axis with respect to the top 31 are obtained by specifying the position of the X-ray generation unit 24 and that of the X-ray detection unit 26. Data of relative positions are data representing a predetermined position of the X-ray generation unit 24 and a predetermined position of the X-ray detection unit 26 by the top coordinate system. Note that data of relative positions may be represented by the machine coordinate system.

Data of relative positions are not limited to the above-mentioned data as long as the data represent the position and direction of the imaging axis with respect to the top 31. For example, data of relative positions may be data representing the position of the arm gantry 2 and that of the top gantry 2 by an examination room coordinate system. The examination room coordinate system is a fixed coordinate system using a predetermined position as the origin in the examination room where the arm gantry 2 and the top gantry 3 are arranged. Further, data of relative positions may be data of an image captured by a camera when the arm gantry 2 and the top gantry 3 have a relative positional relationship. Data of relative positions are output from the position specifying unit 43 (to be described later).

The position specifying unit 43 specifies the mechanical positional relationship between the arm gantry 2 and the top gantry 3. In other words, the position specifying unit 43 specifies the position of each of the plurality of mechanisms constituting the arm gantry 2 with respect to the position of each of the plurality of mechanisms constituting the top gantry 3. The first and second methods are proposed as methods of specifying the mechanical positional relationship between the arm gantry 2 and the top gantry 3.

The first method will be described first.

In the first method, the position specifying unit 43 specifies the mechanical positional relationship between the arm gantry 2 and the top gantry 3 by specifying the position of the arm gantry 2 and the position of the top gantry 3 in the examination room. The position specifying unit 43 includes a C-arm position specifying unit 431 and a top position specifying unit 432. The C-arm position specifying unit 431 specifies the position of the arm gantry 2 in the examination room. More specifically, the C-arm position specifying unit 431 specifies the examination room coordinates of each of a plurality of positions on the arm gantry 2. The top position specifying unit 432 specifies the position of the top gantry 3 in the examination room. More specifically, the top position specifying unit 432 specifies the examination room coordinates of each of a plurality of positions on the top gantry 3. A method of specifying examination room coordinates corresponding to a specific position in the examination room will be explained. In this explanation, a method of specifying a position P of the arm gantry 2 by the C-arm position specifying unit 431 will be mainly explained in order to omit a repetitive description.

The specifying method includes (1) a method using a camera image, (2) a method using a GPS (Global Positioning System), and (3) a method using an ultrasonic system. The respective methods will be explained with reference to FIGS. 4, 5, and 6. FIGS. 4, 5, and 6 show states in which the arm gantry 2 and the top gantry 3 are arranged in the examination room.

(1) Method Using Camera

The C-arm position specifying unit 431 includes a plurality of cameras for specifying the position of the arm gantry 2 on the examination room coordinates. The plurality of cameras are preferably provided at positions capable of imaging from a plurality of directions. An image in the examination room that has been captured by the camera will be called an examination room image. The plurality of cameras may be shared between the C-arm position specifying unit 431 and the top position specifying unit 432. Note that the plurality of cameras may be external cameras. In this case, the X-ray diagnostic apparatus according to the first embodiment is configured to include a reception unit (not shown) for receiving data of an examination room image from the external camera.

Figure 4A:
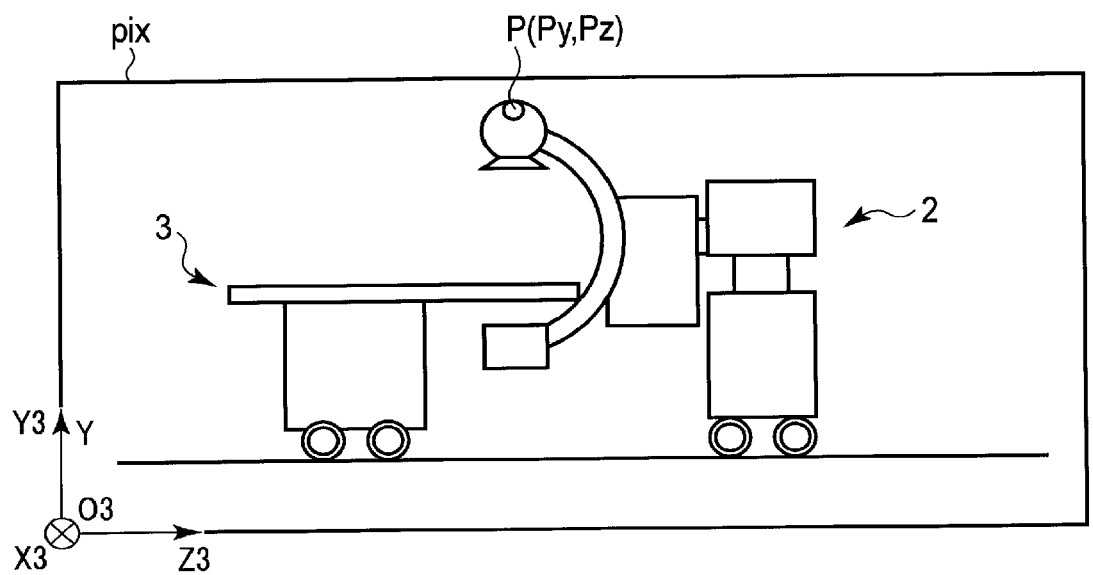
FIG. 4A is a view showing an example of an examination room image corresponding to the first direction.

FIG. 4A is a view showing an example of an examination room image corresponding to the first direction. The origin of the examination room coordinate system is a position O3 in the examination room. The first direction is the X3 direction of the examination room coordinate system. At this time, the camera is arranged in the examination room so that the imaging direction becomes the X3 direction. The C-arm position specifying unit 431 specifies a Y-coordinate Py and Z-coordinate Pz of the position P on the examination room coordinates by extracting the position P of the arm gantry 2 by image processing such as threshold processing from an examination room image pix shown in FIG. 4A. The position P is a characteristic position on the arm gantry 2. The characteristic position may be, for example, a position at which the outer shape of the arm gantry 2 can be grasped, such as the edge and corner of the arm gantry 2, or the position of a characteristic component of the arm gantry 2. Note that the characteristic position may be a mark attached to the arm gantry 2. The mark is a mark which can be extracted by threshold processing from an examination room image. For example, the mark is attached to the arm gantry 2 by the user or the like.

Figure 4B:
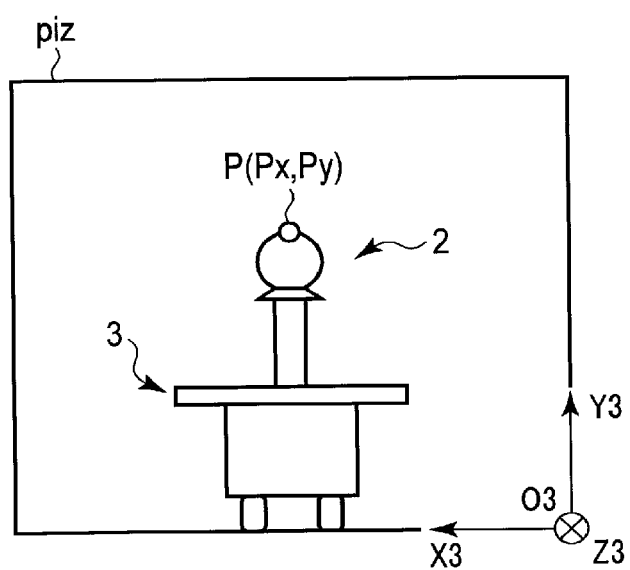
FIG. 4B is a view showing an example of an examination room image corresponding to the second direction.

FIG. 4B is a view showing an example of an examination room image corresponding to the second direction. The second direction is the Z3 direction of the examination room coordinate system. At this time, the C-arm position specifying unit 431 specifies an X-coordinate Px and Y-coordinate Py of the position P on the examination room coordinates based on an examination room image piz shown in FIG. 4B.

By the above-described processing, the C-arm position specifying unit 431 can specify the examination room coordinates (Px, Py, Pz) of the position P of the arm gantry 2 based on the examination room image. Note that when a doctor in the examination room, or a drip, injector device, or the like arranged in the examination room is captured in the examination room image, the C-arm position specifying unit 431 may not be able to extract the position P (feature point) of the arm gantry 2 from the examination room image. Thus, as the number of types of examination room images corresponding to different imaging directions increases, the C-arm position specifying unit 431 can specify the position P at higher accuracy.

Note that the position specifying unit 43 may specify, from an examination room image, the examination room coordinates of the positions of a man and thing other than the arm gantry 2 and the top gantry 3. The specified data is used to generate interference data by the interference data generation unit 45 (to be described later).

(2) Method Using GPS

FIG. 5 is an explanatory view for explaining the method of specifying the position of the arm gantry 2 by the C-arm position specifying unit 431 when the GPS is used. In the GPS, the longitude, latitude, altitude, and the like of a position at which a GPS receiver is arranged are calculated by receiving, by the GPS receiver, radio waves transmitted from each of a plurality of GPS satellites GTx. The C-arm position specifying unit 431 specifies the coordinates of the position P based on an output from a GPS receiver arranged at the position P of the arm gantry 2. The coordinates of the position P at this time are represented by a GPS coordinate system. To transform the coordinates of the position P from the GPS coordinate system into the examination room coordinate system, a conversion table or the like is used. The conversion table is a table for converting GPS coordinates into examination room coordinates, and is stored in advance in the storage unit 46. The examination room coordinates (Gx1, Gy1, Gz1) of the position P can be specified by setting one fixed point in the examination room as a reference position, and calculating differences in longitude, latitude, altitude, and the like from the reference position. The fixed point at this time is, e.g., the origin of the examination room coordinate system.

(3) Method Using Ultrasonic System

An ultrasonic system uses an ultrasonic generator and an ultrasonic receiver. The ultrasonic receiver receives ultrasonic waves generated by the ultrasonic generator. The distance from the ultrasonic generator to the ultrasonic receiver is specified based on the time from generation to reception. By receiving ultrasonic waves generated from the ultrasonic generator by three or more ultrasonic receivers, the three-dimensional coordinates of the ultrasonic generator can be specified.

FIG. 6 is an explanatory view for explaining the method of specifying the position of the arm gantry 2 by the C-arm position specifying unit 431 when the ultrasonic system is used. Referring to FIG. 6, an ultrasonic generation tag is attached at the position P on the arm gantry 2. In addition, ultrasonic receivers are attached to three positions (R1, R2, and R3) in the examination room, respectively. The C-arm position specifying unit 431 specifies the coordinates (Tx1, Ty1, Tz1) of the position P of the arm gantry 2 based on outputs from the ultrasonic receivers R1, R2, and R3. More specifically, each of the ultrasonic receivers R1, R2, and R3 receives ultrasonic waves generated from the ultrasonic generation tag arranged at the position P of the arm gantry 2. Each of the ultrasonic receivers R1, R2, and R3 specifies a distance to the ultrasonic generation tag. The C-arm position specifying unit 431 specifies the examination room coordinates (Tx1, Ty1, Tz1) of the position P by performing trilateration based on an output from each of the ultrasonic receivers.

According to the first method among the above-described three types, the position specifying unit 43 can specify the examination room coordinates of a specific position in the examination room. The position specifying unit 43 specifies the mechanical positional relationship between the arm gantry 2 and the top gantry 3 based on the examination room coordinates of each of a plurality of positions on the arm gantry 2 and the examination room coordinates of each of a plurality of positions on the top gantry 3.

Next, how to set each of a plurality of positions on the arm gantry 2 and the top gantry 3 will be explained with reference to FIGS. 7 and 8. Each of a plurality of positions may be set on one of the plurality of mechanisms constituting the arm gantry 2, or a plurality of positions may be set on the plurality of mechanisms.

FIG. 7A is a view showing the first example of a plurality of positions on the arm gantry 2 of the X-ray diagnostic apparatus according to the first embodiment. Referring to FIG. 7A, the C-arm position specifying unit 431 specifies the examination room coordinates of each of three positions (positions C1, C2, and C3) on the C-arm 21. Of the three positions, the position C1 is set at the upper end of the C-arm 21, the position C2 is set at the center of the C-arm 21, and the position C3 is set at the lower end of the C-arm 21. The position specifying unit 43 specifies the position of the C-arm 21 based on the examination room coordinates of each of the three positions on the C-arm 21. Based on the position of the C-arm 21, the position specifying unit 43 can specify the position of each of the plurality of mechanisms constituting the arm gantry 2. This is because the position specifying unit 43 holds, as data, the positional relationship between the plurality of mechanisms in the arm gantry 2. More specifically, the position specifying unit 43 grasps, based on an output from the arm control unit 501, an amount by which the C-arm 21 has been rotated from its reference position, an arrangement position to which the C-arm 21 has been vertically moved from its reference position, and the like. This is because the arm control unit 501 manages the rotation amount, moving amount, and the like of each driving unit. It therefore suffices to set a plurality of positions on at least one of the plurality of mechanisms constituting the arm gantry 2.

FIG. 7B is a view showing the second example of a plurality of positions on the arm gantry 2 of the X-ray diagnostic apparatus according to the first embodiment. Referring to FIG. 7B, three positions (positions C4, C5, and C6) are distributed and set on a plurality of mechanisms. The position C4 is set on the C-arm holder 221, the position C5 is set on the first support 223, and the position C6 is set on the C-arm support cart 23. As described above, the C-arm position specifying unit 431 grasps the positional relationship between the plurality of mechanisms constituting the arm gantry 2. By specifying the examination room coordinates of each of the three positions, the position specifying unit 43 can specify the position of each of the plurality of mechanisms constituting the arm gantry 2.

FIG. 8 is a view showing an example of a plurality of positions on the top gantry 3 of the X-ray diagnostic apparatus according to the first embodiment. Referring to FIG. 7B, the top position specifying unit 432 specifies the examination room coordinates of each of three positions (positions C7, C8, and C9) on the top 31. The three positions are set at different corners of the top 31, respectively. The position specifying unit 43 specifies the position of the top 31 based on the examination room coordinates of each of the three positions on the top 31. Based on the position of the top 31, the position specifying unit 43 can specify the position of each of the plurality of mechanisms constituting the top gantry 3. This is because the position specifying unit 43 holds, as data, the positional relationship between the plurality of mechanisms in the top gantry 3. More specifically, the position specifying unit 43 grasps, based on an output from the top control unit 502, an amount by which the top 31 has been rotated from its reference position, an arrangement position to which the top 31 has been vertically moved from its reference position, and the like. This is because the top control unit 502 manages the rotation amount, moving amount, and the like of each driving unit. It suffices to set a plurality of positions on at least one of the plurality of mechanisms constituting the top gantry 3. As described above, each of the plurality of positions may be set on one of the plurality of mechanisms constituting the top gantry 3, or the plurality of positions may be distributed and set on the plurality of mechanisms.

In short, the C-arm position specifying unit 431 can specify the examination room coordinates of each of the plurality of positions on the arm gantry 2 on the examination room coordinates. The position specifying unit 43 can specify the position of each of the plurality of mechanisms constituting the arm gantry 2 on the examination room coordinates. The arm gantry 2 has the machine coordinate system serving as the reference to determine the operation direction of the arm gantry 2. The C-arm position specifying unit 431 can specify the positional relationship between the examination room coordinate system and the machine coordinate system. The C-arm position specifying unit 431 can therefore specify the position and direction of the imaging axis on the examination room coordinates.

The top position specifying unit 432 can specify the examination room coordinates of each of the plurality of positions on the top gantry 3 on the examination room coordinates. The position specifying unit 43 can specify the position of each of the plurality of mechanisms constituting the top gantry 3 on the examination room coordinates. The top gantry 3 has the top coordinate system serving as the reference to determine the operation direction of the top gantry 3. The top position specifying unit 432 can specify the positional relationship between the examination room coordinate system and the machine coordinate system. Thus, the top position specifying unit 432 can specify the position and direction of the top 31 on the examination room coordinates.

That is, the position specifying unit 43 can specify the mechanical positional relationship between the arm gantry 2 and the top gantry 3. In other words, the position specifying unit 43 can specify the positional relationship between the machine coordinate system and the top coordinate system. As a result, the position specifying unit 43 can specify the position and direction of the imaging axis with respect to the top 31.

Next, the second method will be explained. The second method is a method of specifying the relative position of the arm gantry 2 with respect to the top gantry 3.

The ultrasonic system described with reference to FIG. 6 has an arrangement in which the ultrasonic receiver is arranged in the examination room and the ultrasonic generation tags are arranged on the arm gantry 2 and the top gantry 3. However, the arrangement of the ultrasonic system is not limited to this. For example, the ultrasonic system may have an arrangement in which an ultrasonic generation tag is arranged at each of a plurality of positions on the top gantry 3, and an ultrasonic receiver is arranged at each of a plurality of positions on the arm gantry 2. According to this ultrasonic system, the position specifying unit 43 can specify each of the plurality of positions on the top gantry 3 with respect to each of the plurality of positions on the arm gantry 2 based on an output from each of the plurality of ultrasonic receivers arranged on the arm gantry 2. The position specifying unit 43 can specify the position of each of the plurality of mechanisms constituting the arm gantry 2 with respect to each of the plurality of mechanisms constituting the top gantry 3. That is, the mechanical positional relationship between the arm gantry 2 and the top gantry 3 can be specified, as in the first embodiment. In other words, the position specifying unit 43 can specify the positional relationship between the machine coordinate system and the top coordinate system. The position specifying unit 43 can specify the position and direction of the imaging axis with respect to the top 31.

In the above description, for example, the C-arm position specifying unit 431 specifies the plurality of positions on the arm gantry 2. This is because the direction in which the arm gantry 2 is oriented cannot be specified from one position. If the direction in which the arm gantry 2 is oriented can be specified, a plurality of positions may not be set on the arm gantry 2. For example, a mark (to be referred to as a three-dimensional mark hereinafter) capable of specifying three axial directions can be arranged at one portion of the arm gantry 2. By specifying the position of the three-dimensional mark of the arm gantry 2 on the examination room coordinates, the C-arm position specifying unit 431 can specify the position of the arm gantry 2 on the examination room coordinates. This also applies to the top position specifying unit 432. More specifically, the position specifying unit 43 can specify the mechanical positional relationship between the arm gantry 2 and the top gantry 3 based on the position of the three-dimensional mark on the examination room coordinates that is attached to each of the arm gantry 2 and top gantry 3, but based on one position on each of the arm gantry 2 and top gantry 3.

Data concerning the mechanical positional relationship between the arm gantry 2 and the top gantry 3 that is specified by the position specifying unit 43 is applied to generation of interference data (to be described later), and alignment between the arm gantry 2 and the top gantry 3, preset registration, and the like at the time of executing the auto-positioning function.

The interference data generation unit 45 generates interference data based on an output from the position specifying unit 43. The interference data is data representing the mechanical positional relationship between the arm gantry 2 and the top gantry 3. More specifically, the interference data includes position data of each of the plurality of mechanisms constituting the arm gantry 2 on the examination room coordinates, and position data of each of the plurality of mechanisms constituting the top gantry 3 on the examination room coordinates. The interference data may be data representing a distance and direction from each of the plurality of mechanisms constituting the arm gantry 2 to each of the plurality of mechanisms constituting the top gantry 3. When the positions, on the examination room coordinates, of obstacles such as a man and thing other than the arm gantry 2 and the top gantry 3 have been specified, the interference data may be data representing the mechanical positional relationship between the arm gantry 2 and the obstacles and between the top gantry 3 and the obstacles. The interference data is data used to limit the moving ranges of the arm gantry 2 and top gantry 3. By limiting the moving range of each of the arm gantry 2 and top gantry 3, contact between the arm gantry 2 and the top gantry 3, contact between the arm gantry 2 and the obstacles, and contact between the top gantry 3 and the obstacles can be prevented. Hence, the interference data may be data representing the movable range of each of the arm gantry 2 and top gantry 3. The movable ranges of the arm gantry 2 and top gantry 3 are moving ranges in which the mechanisms constituting the arm gantry 2 and the mechanisms constituting the top gantry 3 do not contact each other.

The display unit 48 displays an X-ray image generated by the image generation unit 42 on a display screen. The display unit 48 displays a message on the display screen based on an output from the imaging control unit 50.

The system control unit 49 receives information input from the input unit 47, and temporarily stores the input information in memory circuitry. The system control unit 49 controls each unit of the X-ray diagnostic apparatus based on this input information.

The imaging control unit 50 controls each unit in order to perform X-ray imaging in response to pressing of the imaging switch of the input unit 47. More specifically, the imaging control unit 50 controls the high voltage generation unit 25 and the X-ray detection unit 26 in order to image an object in accordance with imaging conditions set by the user. Under the control of the imaging control unit 50, the high voltage generation unit 25 and the X-ray detection unit 26 are synchronized, and the imaging operation is executed.

Also, the imaging control unit 50 controls each driving unit in order to move the arm gantry 2 and the top gantry 3 in accordance with a user instruction via the input unit 47. At this time, the imaging control unit 50 limits the moving range of each of the arm gantry 2 and top gantry 3 based on interference data generated by the interference data generation unit 45. Before the arm gantry 2 and the top gantry 3 contact each other, the imaging control unit 50 outputs a movement stop signal to at least one of the arm control unit 501 and top control unit 502. The time before the contact is, e.g., a timing when the distance between each of the plurality of mechanisms constituting the arm gantry 2 and each of the plurality of mechanisms constituting the top gantry 3 becomes equal to or smaller than a threshold. The imaging control unit 50 outputs, to the display unit 48, data of a message notifying the user that the movement has been stopped and that the arm gantry 2 and the top gantry 3 will contact each other if they are further moved. Note that the imaging control unit 50 may invalidate a user operation via the input unit 47 so as to prevent contact between the arm gantry 2 and the top gantry 3. If the interference data includes data concerning obstacles in the examination room, the imaging control unit 50 may limit the moving range of each of the arm gantry 2 and top gantry 3 so that the arm gantry 2 and the top gantry 3 do not contact the obstacles in the examination room.

The imaging control unit 50 executes the following auto-positioning processing in response to pressing of the preset button. The auto-positioning processing of the X-ray diagnostic apparatus according to the first embodiment will be explained below.

(Preparation for Auto-Positioning Function)

The user performs preset registration of the positional relationship between the arm gantry 2 and the top gantry 3. The procedures of preset registration are as follows.

First, the user moves the arm gantry 2 and the top gantry 3 via the input unit 47 to positions at which he wants to perform present registration. Then, the user presses long a preset button provided on the input unit 47. In response to this, data of relative positions representing the position and direction of the imaging axis with respect to the top 31 are registered in association with the long-pressed preset button. The storage unit 46 stores the preset button and data of the corresponding relative positions in association with each other.

(Execution of Auto-Positioning Function)

The auto-positioning function according to the first embodiment is a function of automatically moving the arm gantry 2 and the top gantry 3 so that the positional relationship between the arm gantry 2 and the top gantry 3 separately arranged without intention is changed to the relationship of relative positions corresponding to a preset button pressed by the user. Processing (to be referred to as auto-positioning processing hereinafter) concerning the auto-positioning function will be described with reference to FIGS. 9 and 10.

Figure 9:
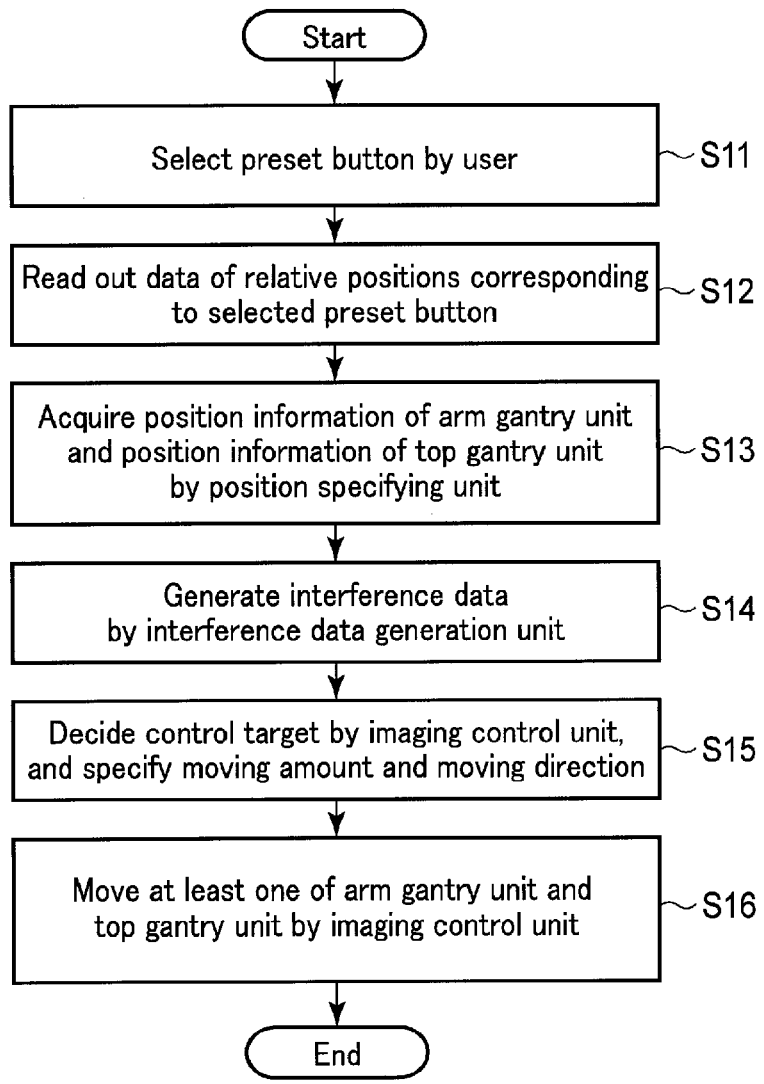
FIG. 9 is a flowchart for explaining the sequence of auto-positioning processing of the X-ray diagnostic apparatus according to the first embodiment.

FIG. 9 is a flowchart for explaining the sequence of auto-positioning processing of the X-ray diagnostic apparatus according to the first embodiment. A sequence until at least one of the arm gantry 2 and top gantry 3 is moved so that the imaging axis is changed from a position in FIG. 10B to a position in FIG. 10A with respect to the top 31 by the auto-positioning function will be explained with reference to FIG. 9. Assume that the user such as a doctor arranges the arm gantry 2 at a position in a certain range with respect to the top gantry 3. The position in a certain range is a state in which the insertion direction of the C-arm 21 with respect to the top 31 is determined.

Figure 10A:
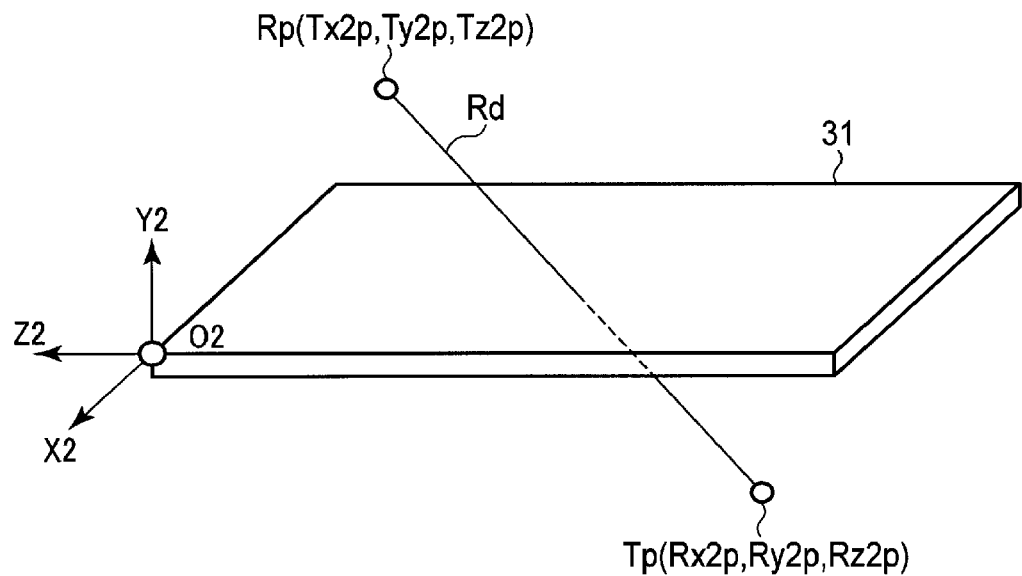
FIG. 10A is a view showing the position of an imaging axis with respect to a top that is registered in a preset button.

FIG. 10A is a view showing the position of an imaging axis Rdp with respect to the top 31 that is registered in a preset button. Referring to FIG. 10A, the position of the imaging axis Rdp is indicated by a position Tp of the X-ray focus of the X-ray generation unit 24 and a center position Rp of the X-ray detection surface of the X-ray detection unit 26. Each of the positions Tp and Rp is represented by the top coordinate system using a predetermined position of the top 31 as the origin.

Figure 10B:
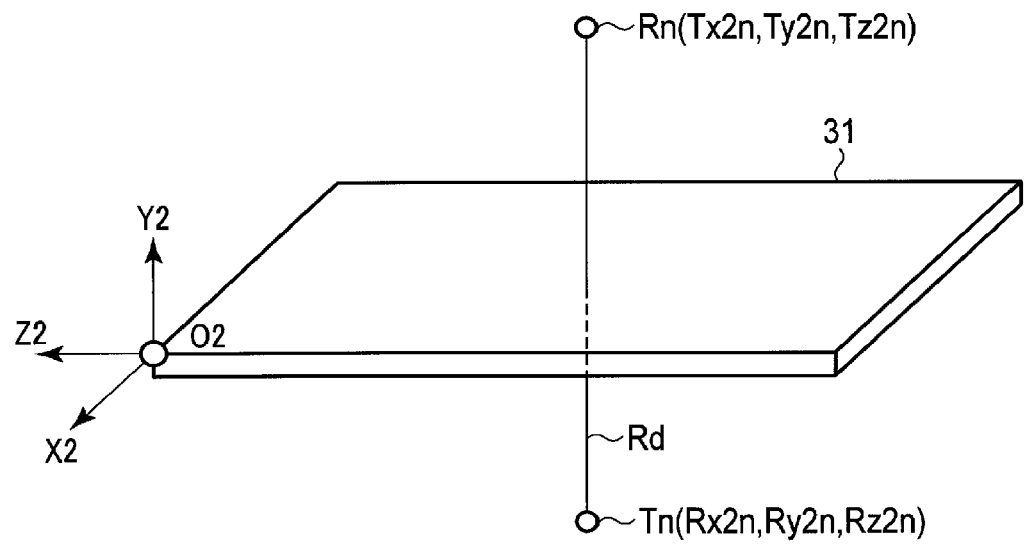
FIG. 10B is a view showing the current position of the imaging axis with respect to the top.

FIG. 10B is a view showing the current position of an imaging axis Rdn with respect to the top 31. Referring to FIG. 10B, the imaging axis Rdn is indicated by a position Tn of the X-ray focus of the X-ray generation unit 24 and a center position Rn of the X-ray detection surface of the X-ray detection unit 26.

Auto-positioning processing will be explained with reference to the flowchart of FIG. 9.

(Step S11)

The user selects one of a plurality of preset buttons.

(Step S12)

Data of relative positions corresponding to the selected preset button are read out from the storage unit 46 under the control of the system control unit 49. Referring to FIG. 10A, data of the positions Tp and Rp are read out from the storage unit 46.

(Step S13)

Based on the position information of the arm gantry 2 and the position information of the top gantry 3, the position specifying unit 43 specifies the current positional relationship between the arm gantry 2 and the top gantry 3. More specifically, the current positional relationship of the imaging axis Rdn with respect to the top 31 is specified. As a result, for example, the examination room coordinates of the positions Tn and Rn shown in FIG. 10B are specified.

(Step S14)

The interference data generation unit 45 generates interference data based on the positional relationship between the arm gantry 2 and the top gantry 3 that has been specified in step S13.

(Step S15)

The imaging control unit 50 specifies the moving amount and moving direction of at least one of the arm gantry 2 and top gantry 3 so that the current positional relationship of the imaging axis Rdn with respect to the top 31 is changed to a positional relationship of the imaging axis Rdp with respect to the top 31 that is registered in the preset button. Accordingly, for example, parameters (moving amount and moving direction) for causing the current positions Tn and Rn (and the imaging axis Rdn) to respectively coincide with the positions Tp and Rp (and the imaging axis Rdp) registered in the preset button in FIG. 10B are specified. At this time, the imaging control unit 50 decides a preferential control target among the arm gantry 2 and the top gantry 3 based on the control priority and the interference data. For example, assume that the control priority of the top gantry 3 is set to be "low" on the assumption that a patient is placed on the top 31 and it is desirable not to move the top gantry 3. The safety of the patient can therefore be ensured at the time of executing the auto-positioning function. At this time, the imaging control unit 50 specifies the moving amount and moving direction of each of the plurality of mechanisms constituting the arm gantry 2. For example, when the arm gantry 2 cannot be moved, the control priority of the top gantry 3 is set to be high.

(Step S16)

The imaging control unit 50 moves at least one of the arm gantry 2 and top gantry 3. More specifically, the imaging control unit 50 outputs, to at least one of the arm control unit 501 and top control unit 502, a movement control signal corresponding to the moving amount and moving direction decided and specified in step S15. At this time, a movement control signal to be output to the arm control unit 501 includes movement instruction information in the machine coordinate system. To the contrary, a movement control signal to be output to the top control unit 502 includes movement instruction information in the top coordinate system. The arm control unit 501 can move the arm gantry 2, and the top control unit 502 can move the top gantry 3.

By the processing from steps S11 to S16, alignment of the imaging axis is completed, and auto-positioning is ended. A case is assumed here, in which the user such as a doctor arranges the arm gantry 2 at a position in a certain range with respect to the top gantry 3. However, the auto-positioning function is usable even in a state in which the insertion direction of the C-arm 21 with respect to the top 31 has not been determined, that is, a case in which the arm gantry 2 and the top gantry 3 are arranged at a large interval between them. At this time, in step S15, the imaging control unit 50 performs processing such as decision of the insertion direction of the C-arm 21 with respect to the top 31. A method of deciding the insertion direction of the C-arm 21 with respect to the top 31 will be explained with reference to FIG. 11.

Figure 11:
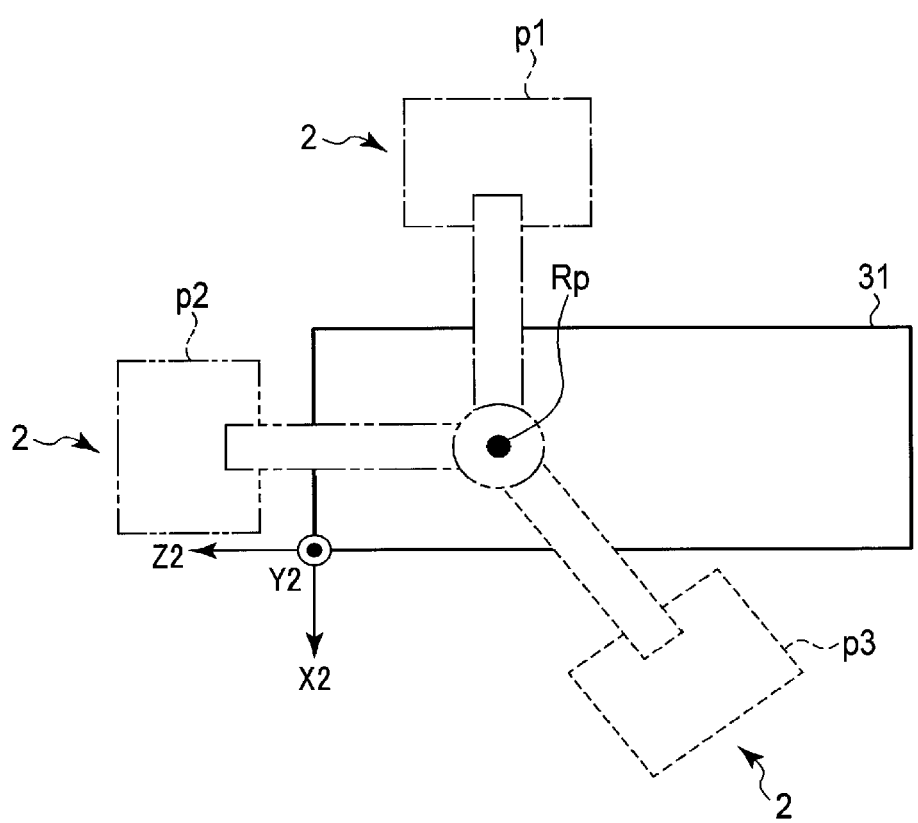
FIG. 11 is an explanatory view for explaining a method of deciding the insertion direction of a C-arm with respect to the top.

FIG. 11 is an explanatory view for explaining the method of deciding the insertion direction of the C-arm 21 with respect to the top 31. FIG. 11 is a view of the top 31 when viewed from the front (direction of the axis Y2 of the top coordinate system). FIG. 11 shows an example of a plurality of patterns each representing a state in which the current position Rn of the X-ray focus of the X-ray generation unit 24 is arranged at the arrangement target position Rp. The imaging axis is an axis parallel to the axis Y2 in all patterns. A pattern p1 represents a state in which the C-arm 21 is inserted from the short-axis direction (X2 direction) of the top 31. A pattern p2 represents a state in which the C-arm 21 is inserted from the long-axis direction (Z2 direction) of the top 31. A pattern p3 represents a state in which the C-arm 21 is inserted from the oblique direction of the top 31. That is, there are several patterns for arranging the arm gantry 2 with respect to the top gantry 3 in order to arrange the current imaging axis Rdn to the arrangement target imaging axis Rdp. For example, the imaging control unit 50 decides a position at which the arm gantry 2 is arranged with respect to the top gantry 3, so as to minimize the total moving distances of the arm gantry 2 and top gantry 3 based on the positional relationship between the arm gantry 2 and the top gantry 3. Note that the C-arm 21 is generally inserted from the head or side of a patient. Thus, the imaging control unit 50 may decide the arrangement at a position for inserting the C-arm 21 from the head of the patient or a position for inserting the C-arm 21 from the side of the patient. The position at which the arm gantry 2 is arranged may be decided in accordance with a user instruction. At this time, the display unit 48 displays, e.g., a plurality of arrangement candidates as marks on the schematic view of the top 31 when viewed from the front, as shown in FIG. 11. The user can view the displayed schematic view and select, from the plurality of arrangement candidates, a position at which the arm gantry 2 is arranged with respect to the top gantry 3. Note that the schematic view may be an image captured by a camera. Also, the imaging control unit 50 may decide the arrangement of the arm gantry 2 with respect to the top gantry 3 based on interference data. More specifically, the imaging control unit 50 decides the arrangement of the arm gantry 2 with respect to the top gantry 3 so as not to obstruct the user such as a doctor, medical equipment, and the like. The method of moving the arm gantry 2 with respect to the top gantry 3 while fixing the top gantry 3 at the current position, and the method of moving the top gantry 3 with respect to the arm gantry 2 while fixing the arm gantry 2 at the current position have been mainly described above. However, each of the arm gantry 2 and top gantry 3 can be moved to a desired position in the examination room. At this time, for example, the display unit 48 displays the layout view of the examination room. On the displayed layout view of the examination room, the user can designate a position at which the top 31 is arranged, and the insertion direction of the C-arm 21 with respect to the top 31.

The auto-positioning function of the X-ray diagnostic apparatus according to the first embodiment has the following effects. By using the X-ray diagnostic apparatus according to the first embodiment, the arm gantry 2 and the top gantry 3 not having undergone intentional alignment can be automatically moved to relative positions corresponding to a preset button pressed by the user. In this movement, the arm gantry 2 can be arranged with respect to the top gantry 3 while the top gantry 3 is fixed at the current position. Also, the top gantry 3 can be arranged with respect to the arm gantry 2 while the arm gantry 2 is fixed at the current position. Each of the arm gantry 2 and top gantry 3 can be arranged at a desired position in the examination room. This can increase the degree of freedom of the arrangement method of the arm gantry 2 and top gantry 3 in the examination room. Since alignment can be performed easily every time the X-ray diagnostic apparatus is used, the improvement of the workflow can be expected.

The X-ray diagnostic apparatus according to the first embodiment moves the arm gantry 2 and the top gantry 3 in an order complying with the control priority. The control priority can be properly changed in accordance with a user instruction. By setting the control priority, the user can designate a mechanism to be preferentially moved among the arm gantry 2 and the top gantry 3. This can decrease the risk of movement with danger in which, for example, the top gantry 3 is greatly moved while a patient is placed on the top 31. The X-ray diagnostic apparatus according to the first embodiment limits the moving range of each of the arm gantry 2 and top gantry 3 in accordance with interference data. By limiting the moving range, contact between the arm gantry 2 and the top gantry 3, contact between the arm gantry 2 and obstacles, and contact between the top gantry 3 and obstacles can be prevented.

As described above, the X-ray diagnostic apparatus according to the first embodiment including at least the portable C-arm 21 or the portable top 31 can easily move the C-arm 21 to a desired position. In other words, the X-ray diagnostic apparatus according to the second embodiment including at least the portable C-arm 21 or the portable top 31 can easily align an object with respect to an imaging position.

In the first embodiment, the positional relationship between the arm gantry 2 and the top gantry 3 can be changed to a relationship between relative positions registered in advance. However, by applying the arrangement of an object position specifying unit 433 according to the third embodiment (to be described later) to the first embodiment, the positional relationship between the arm gantry 2 and a patient can be changed to a relationship between relative positions registered in advance. Main processing of each constituent unit is the same as that in the first embodiment. The difference at this time is as follows. The storage unit 46 stores data of relative positions representing the relationship between the relative positions of the arm gantry 2 and a patient. The position specifying unit 43 can specify the positional relationship between the arm gantry 2 and the patient based on a plurality of positions on the arm gantry 2 and a plurality of positions on the patient in the examination room. The imaging control unit 50 can move the arm gantry 2 with respect to the patient so as to obtain the relationship between relative positions corresponding to a preset button. In this manner, for example, the arm gantry 2 can be easily aligned to a patient placed on a stretcher or the like, other than the predetermined top gantry 3.

(Modification)

In auto-positioning processing of the X-ray diagnostic apparatus according to the first embodiment, at least one of the arm gantry 2 and top gantry 3 is automatically moved. However, the user may manually move at least one of the arm gantry 2 and top gantry 3.

An X-ray diagnostic apparatus according to a modification of the first embodiment displays, on the display unit 48, an assistant image for changing the positional relationship between the arm gantry 2 and the top gantry 3 to a positional relationship corresponding to a preset button. The assistant image includes text information about the moving direction and moving amount of each of the arm gantry 2 and top gantry 3 that are necessary to change the arm gantry 2 and the top gantry 3 from the current positional relationship to a relationship between relative positions corresponding to the preset button. The imaging control unit 50 specifies the moving direction and moving amount of each of the arm gantry 2 and top gantry 3 based on position information of the arm gantry 2, position information of the top gantry 3, and data of relative positions corresponding to a preset button. Information about the moving direction and moving amount of the arm gantry 2 is represented by the machine coordinate system. Information about the moving direction and moving amount of the top gantry 3 is represented by the top coordinate system. For example, when the arm gantry 2 is moved, the moving direction and moving amount corresponding to each of the arm gantry 2 and top gantry 3, which are displayed on the assistant image, are updated. Since the position specifying unit 43 has already specified the positional relationship between the examination room coordinate system, the machine coordinate system, and the top coordinate system, the moving direction and moving amount included in the assistant image can be represented by any of these coordinate systems. For example, information about the moving direction and moving amount of each of the arm gantry 2 and top gantry 3 may be represented by a common coordinate system, for example, the examination room coordinate system. Which of an individual coordinate system and common coordinate system represents information can be properly changed in accordance with a user instruction. The common coordinate system is selected from the examination room coordinate system, the machine coordinate system, and the top coordinate system in accordance with a user instruction.

The input unit 47 includes a selection switch for selecting the manual mode and the automatic mode at the time of executing the auto-positioning function. When the manual mode is selected, the display unit 48 displays an assistant image (modification of the first embodiment). In contrast, when the automatic mode is selected, the arm gantry 2 and the top gantry 3 are automatically moved (first embodiment).

The X-ray diagnostic apparatus according to the modification of the first embodiment has the following effects. The X-ray diagnostic apparatus according to the modification of the first embodiment can display the moving direction and moving amount of each of the arm gantry 2 and top gantry 3 that are necessary to change the arm gantry 2 and the top gantry 3 into a positional relationship corresponding to a preset button. While viewing the assistant image, the user can move each of the arm gantry 2 and top gantry 3 to change the positional relationship between the arm gantry 2 and the top gantry 3 to a positional relationship corresponding to a preset button. At this time, movement information (moving direction and moving amount) of each of the arm gantry 2 and top gantry 3, which is included in the assistant image, is displayed by a coordinate system complying with a user instruction. For example, when the user manually moves the arm gantry 2 and the top gantry 3, it is preferable to display movement information of each of the arm gantry 2 and top gantry 3 by a common coordinate system, for example, the examination room coordinate system. This is because the user can operate the arm gantry 2 and the top gantry 3 on the common coordinates. The user can easily move the arm gantry 2 and the top gantry 3, compared to a case in which he moves the arm gantry 2 while viewing movement information represented by the machine coordinate system, and moves the top gantry 3 while viewing movement information represented by the top coordinate system. When the arm gantry 2 is moved using an operation console for the arm gantry 2 and the top gantry 3 is moved using an operation console for the top gantry 3, it is preferable to display movement information of the arm gantry 2 by the machine coordinate system and movement information of the top gantry 3 by the top coordinate system. In this case, the user can move each of the arm gantry 2 and top gantry 3 by using the dedicated operation console.

As described above, the X-ray diagnostic apparatus according to the modification of the first embodiment including at least the portable C-arm or the portable top can easily move the C-arm to a desired position.

Second Embodiment

Figure 12:
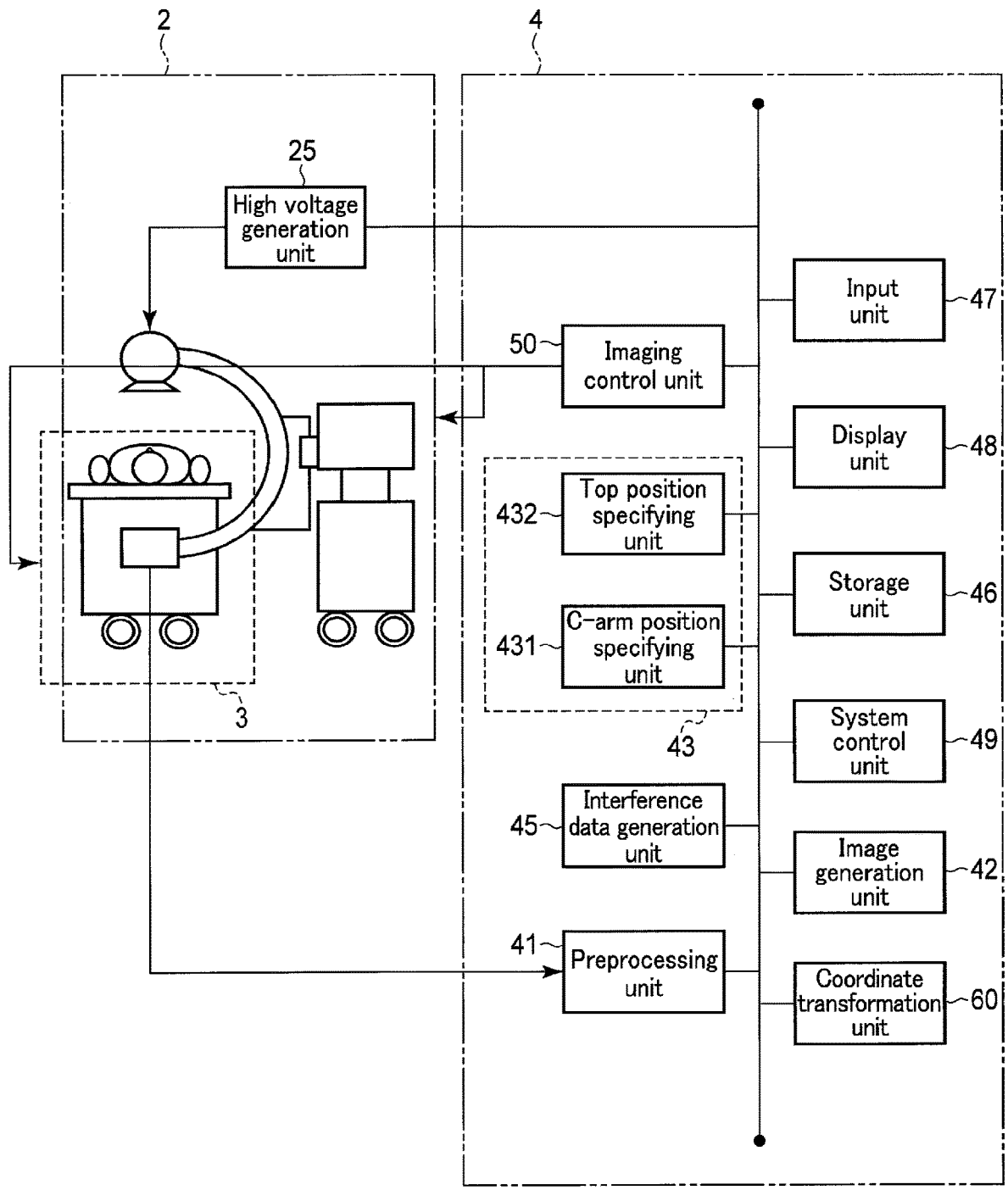
FIG. 12 is a block diagram showing the arrangement of an X-ray diagnostic apparatus according to the second embodiment.

FIG. 12 is a block diagram showing the arrangement of an X-ray diagnostic apparatus according to the second embodiment. The X-ray diagnostic apparatus according to the second embodiment includes a coordinate transformation unit 60. The X-ray diagnostic apparatus according to the first embodiment can automatically move the arm gantry 2 and the top gantry 3 so that the current positional relationship between the arm gantry 2 and the top gantry 3 is changed to a predetermined relationship between relative positions. To the contrary, the X-ray diagnostic apparatus according to the second embodiment can move an arm gantry 2 in accordance with a movement instruction input in the top coordinate system by the user. The X-ray diagnostic apparatus according to the second embodiment will be explained mainly for a difference from the X-ray diagnostic apparatus according to the first embodiment.

Based on the positional relationship between the arm gantry 2 and a top gantry 3, the coordinate transformation unit 60 transforms instruction information about the arm gantry 2 that has been input in the top coordinate system, into one in the machine coordinate system. In other words, the coordinate transformation unit 60 transforms instruction information about the arm gantry 2 that has been input in the top coordinate system, into one in the machine coordinate system based on the positional relationship between the top coordinate system and the machine coordinate system. This is because a coordinate system concerning the operation of the arm gantry 2 and a coordinate system concerning the operation of the top gantry 3 are different and, for example, when the arm gantry 2 operates in accordance with a movement instruction input in the top coordinate system, the arm gantry 2 cannot be moved in a direction intended by the user. This instruction information includes, e.g., a rotation instruction and a translation instruction. The coordinate transformation unit 60 specifies a transformation condition for transforming coordinates in the top coordinate system into those in the machine coordinate system. The transformation condition is, e.g., a coordinate transformation matrix. Here, only transformation from the top coordinate system into the machine coordinate system has been explained. However, since the positional relationship between the examination room coordinate system, the top coordinate system, and the machine coordinate system is known, the coordinate transformation unit 60 can also transform pieces of movement instruction information input in the machine coordinate system, the examination room coordinate system, and the top coordinate system into those in the other coordinate systems.

An imaging control unit 50 outputs, to an arm control unit 501, instruction information transformed into the machine coordinate system by the coordinate transformation unit 60.

FIG. 13 is an explanatory view for explaining processing of the coordinate transformation unit 60 of the X-ray diagnostic apparatus according to the second embodiment. In the top coordinate system, the short-axis direction of a top 31 is an X-axis X2, a direction perpendicular to the top surface of the top 31 is a Y-axis Y2, and the long-axis direction is a Z-axis Z2. The origin of the top coordinate system is fixed in advance at, e.g., a position shown in FIG. 13. In the machine coordinate system, the X-axis is an axis X1 parallel to a rotation axis Rb, the Z-axis is an axis Z1 parallel to a rotation axis Ra, and the Y-axis is an axis Y1 perpendicular to the X-axis X1 and the Z-axis Z1. The origin of the machine coordinate system is set at the isocenter. The origin of the machine coordinate system and that of the top coordinate system are fixed points in the respective apparatuses for descriptive convenience, but may not be fixed points in practice. However, each of the three axial directions in the machine coordinate system and the three axial directions in the top coordinate system needs to be determined with reference to a predetermined position. In other words, the three axial directions serving as a reference for operating the arm gantry 2 are fixed with reference to a predetermined position of the arm gantry 2. The three axial directions serving as a reference for operating the top gantry 3 are fixed with reference to a predetermined position of the top gantry 3.

Figure 13A:
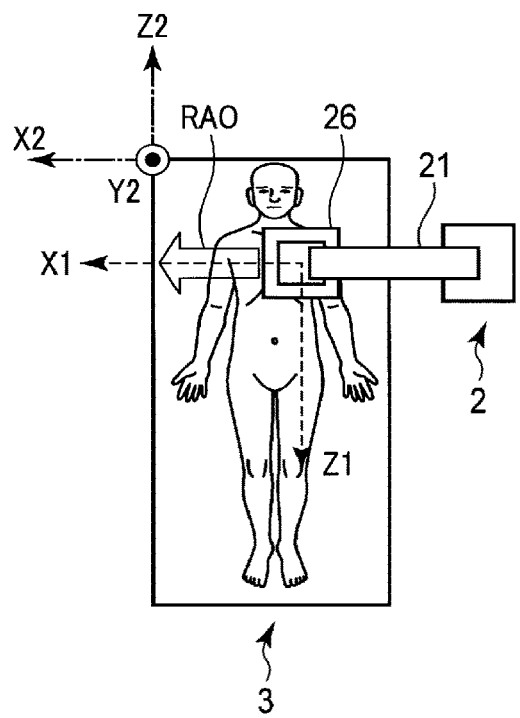
FIG. 13A is a view schematically showing a state in which the C-arm is inserted from the long-axis direction of the top.

FIG. 13A is a view schematically showing a state in which a C-arm 21 is inserted from the long-axis direction of the top 31.

Figure 13B:
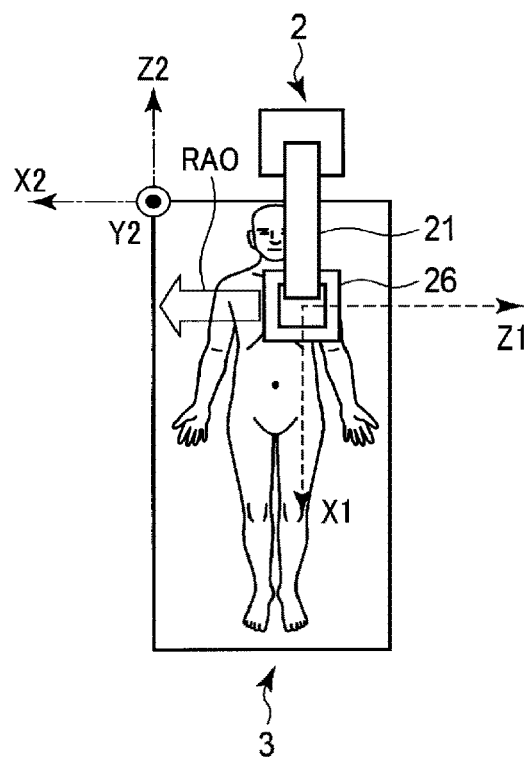
FIG. 13B is a view schematically showing a state in which the C-arm is inserted from the short-axis direction of the top.

FIG. 13B is a view schematically showing a state in which the C-arm 21 is inserted from the short-axis direction of the top 31.

FIG. 13C is a view schematically showing a state in which the C-arm 21 is inserted from a direction oblique to the long- and short-axis directions of the top 31.

FIGS. 13A, 13B, and 13C show postures in which the same region of a patient is imaged. FIGS. 13A, 13B, and 13C schematically show states in which the insertion positions of the C-arm 21 with respect to the top 31 are different. The following description assumes that a patient is placed on the top 31 so that the front direction of the patient becomes parallel to the Y-axis Y2. Also, assume that the control priority of the arm gantry 2 is higher than that of the top gantry 3.

For example, when 20-mm movement in the Z2 direction in the top coordinate system is designated, the imaging control unit 50 and the coordinate transformation unit 60 perform the following processing. Referring to FIG. 13A, the coordinate transformation unit 60 transforms the movement instruction "20 mm in the Z2 direction" input in the top coordinate system into one in the machine coordinate system. The transformed movement instruction is "20 mm in the Z1 direction". The imaging control unit 50 outputs, to the arm control unit 501, a movement control signal for moving the arm gantry 2 by 20 mm in the Z1 direction in the machine coordinate system. Referring to FIG. 13B, the coordinate transformation unit 60 transforms the movement instruction "20 mm in the Z2 direction" input in the top coordinate system into one in the machine coordinate system. The transformed movement instruction is "20 mm in the X1 direction". The imaging control unit 50 outputs, to the arm control unit 501, a movement control signal for moving the arm gantry 2 by 20 mm in the X1 direction in the machine coordinate system. Referring to FIG. 13C, the coordinate transformation unit 60 transforms the movement instruction "20 mm in the Z2 direction" input in the top coordinate system into one in the machine coordinate system. The transformed movement instruction is "20 mm in the D1 direction". The imaging control unit 50 outputs, to the arm control unit 501, a movement control signal for moving the arm gantry 2 by 20 mm in the D1 direction in the machine coordinate system. The D1 direction is a direction parallel to the Z2 direction of the top coordinate system and is represented by the X1 and Z1 directions of the machine coordinate system. In the case of FIG. 13C, the imaging control unit 50 outputs, to the arm control unit 501, a movement control signal for moving the arm gantry 2 in the two axial directions (X1 and Z1 directions). The arm control unit 501 moves the arm gantry 2 in the D1 direction in accordance with the movement control signal output from the imaging control unit 50.

Similarly, when rotation of RAO 20° in the top coordinate system is designated, the imaging control unit 50 and the coordinate transformation unit 60 perform the following processing. Referring to FIG. 13A, the coordinate transformation unit 60 transforms the rotation instruction "RAO 20°" input in the top coordinate system into one in the machine coordinate system. The transformed rotation instruction is "20° about the rotation axis Ra in the +X1 direction". The imaging control unit 50 outputs, to the arm control unit 501, a movement control signal for rotating the C-arm 21 by 20° about the rotation axis Ra in the +X1 direction in the machine coordinate system. Referring to FIG. 13B, the coordinate transformation unit 60 transforms the rotation instruction "RAO 20°" input in the top coordinate system into one in the machine coordinate system. The transformed rotation instruction is "20° about the rotation axis Rb in the −Z1 direction". The imaging control unit 50 outputs, to the arm control unit 501, a movement control signal for rotating the C-arm 21 by 20° about the rotation axis Rb in the −Z1 direction in the machine coordinate system. Referring to FIG. 13C, the coordinate transformation unit 60 transforms the rotation instruction "RAO 20°" input in the top coordinate system into one in the machine coordinate system. The transformed rotation instruction is "XX° about the rotation axis Ra and YY° about the rotation axis Rb". The imaging control unit 50 outputs, to the arm control unit 501, a movement control signal for rotating the C-arm 21 by XX° about the rotation axis Ra in the machine coordinate system and YY° about the rotation axis Rb. Note that XX° and YY° are decided based on the insertion angle of the C-arm 21 with respect to the top 31, and the like. The arm control unit 501 rotates the C-arm 21 in the two axial directions in accordance with the movement control signal from the imaging control unit 50. As a result, the C-arm 21 is rotated by RAO 20°. As described above, the X-ray diagnostic apparatus according to the second embodiment can be used to move the arm gantry 2 based on movement instruction information input in the top coordinate system.

FIG. 14 is a flowchart showing a series of workflow operations when the X-ray diagnostic apparatus according to the second embodiment is used. Referring to FIG. 13, the control priority of the arm gantry 2 is assumed to be higher than that of the top gantry 3.

(Step S21)
The user presses a set button. The set button is a button for allowing the user to input a movement instruction for the arm gantry 2 in the top coordinate system. In other words, a transformation condition is specified in response to pressing of the set button.

(Step S22)
A position specifying unit 43 specifies the positional relationship between the arm gantry 2 and the top gantry 3.

(Step S23)
The coordinate transformation unit 60 specifies the transformation condition.

(Step S24)
The user inputs movement instruction information in the top coordinate system.

(Step S25)
The coordinate transformation unit 60 transforms the movement instruction information input in step S24 into one in the machine coordinate system in accordance with the transformation condition.

(Step S26)
The imaging control unit 50 outputs, to the arm control unit 501, the movement instruction information transformed into the machine coordinate system in step S25.

(Step S27)
The arm control unit 501 receives the movement instruction signal output from the imaging control unit 50. The arm control unit 501 moves the arm gantry 2 in accordance with the movement instruction information transferred into the machine coordinate system.

(Step S28)
If the user presses the imaging switch of the input unit 47, the process shifts to step S29. If the user does not press the imaging switch, the process shifts to step S30. The imaging switch is a switch which triggers X-ray imaging.

(Step S29)
X-ray imaging is performed under the control of the imaging control unit 50.

(Step S30)

The procedures from step S24 to step S29 are repetitively executed until X-ray imaging is ended.

By the procedures in steps S21 to S30, X-ray imaging using the X-ray diagnostic apparatus according to the second embodiment is performed. It has been described in the flow sequence of FIG. 14 that the movement operation of the arm gantry 2 can be input in the top coordinate system in response to pressing of the set button. Alternatively, the processes in steps S22 and S23 may be automatically performed in response to detection of a change of the position of the top gantry 3 in the examination room by the position specifying unit 43.

The X-ray diagnostic apparatus according to the second embodiment has the following effects.

The X-ray diagnostic apparatus according to the second embodiment can transform movement instruction information input in the top coordinate system into one in the machine coordinate system. The X-ray diagnostic apparatus according to the second embodiment can transform pieces of movement instruction information input in the machine coordinate system, the examination room coordinate system, and the top coordinate system into those in the other coordinate systems. Therefore, the X-ray diagnostic apparatus according to the second embodiment can move the arm gantry 2 in accordance with movement instruction information input in the top coordinate system by the user. For example, even when the C-arm 21 is inserted with respect to the top 31 from various directions, as shown in FIGS. 13A, 13B, and 13C, the user can input movement of the arm gantry 2 in the top coordinate system. The user can move the arm gantry 2 with respect to the top gantry 3 without concern for the positional relationship between the arm gantry 2 and the top gantry 3. In other words, the X-ray diagnostic apparatus according to the second embodiment can easily move the C-arm 21 to a desired position.

The X-ray diagnostic apparatus according to the second embodiment including at least the portable C-arm 21 or the portable top 31 can easily align an object with respect to an imaging position.

Third Embodiment

FIG. 15 is a block diagram showing the arrangement of an X-ray diagnostic apparatus according to the third embodiment. The third embodiment is different from the second embodiment in that an object position specifying unit 433 is added in the third embodiment. The X-ray diagnostic apparatus according to the first embodiment can change the current positional relationship between the arm gantry 2 and the top gantry 3 into a predetermined relationship between relative positions. The X-ray diagnostic apparatus according to the second embodiment can move the arm gantry 2 in accordance with a movement instruction input in the top coordinate system. At this time, assuming that a patient is placed on the top 31 in a predetermined posture (e.g., on his/her back) in advance, even if a moving angle is input by a clinical angle, the arm gantry 2 can be moved.

The X-ray diagnostic apparatus according to the third embodiment can move an arm gantry 2 in accordance with a movement instruction input in a clinical coordinate system. Hence, a patient can be placed in an arbitrary posture on a top 31. The X-ray diagnostic apparatus according to the third embodiment will be explained mainly for a difference from the first and second embodiments.

FIG. 16 is a view showing the clinical coordinate system. Referring to FIG. 16, the clinical coordinate system has an origin O4, an axis Y4 parallel to the front direction of a patient, an axis Z4 parallel to the body axis of the patient, and an axis X4 perpendicular to the axes Y4 and Z4.

In the clinical coordinate system, the front direction (axis Y4) of a patient is defined as the base point, a rotation angle toward the right hand of the patient is represented by the first oblique position (Right Anterior Oblique view: to be referred to as RAO hereinafter), and a rotation angle toward the left hand is represented by the second oblique position (Left Anterior Oblique view: to be referred to as LAO hereinafter). Also, the front direction (axis Y4) of the patient is defined as the base point, and a rotation angle in the craniocaudal direction of the patient is represented by the cranial direction (CRAnial: to be referred to as CRA hereinafter) and the caudal direction (CAUdal: to be referred to as CAU hereinafter). Note that RAO, LAO, CRA, and CAU (to be referred to as clinical angles altogether hereinafter) are represented by angles (clinical angles) by setting the front direction (axis Y4) as 0°.

A position specifying unit 43 includes a C-arm position specifying unit 431, a top position specifying unit 432, and the object position specifying unit 433. As described in the first embodiment, the position specifying unit 43 can specify the positional relationship between the arm gantry 2 and a top gantry 3. The position specifying unit 43 according to the third embodiment can specify the positional relationship between the arm gantry 2 and a patient. In other words, the position specifying unit 43 can specify the positional relationship between the machine coordinate system and the clinical coordinate system. Two methods are proposed as the specifying method.

As in the first embodiment, the first method is a method of specifying the positional relationship between the arm gantry 2 and a patient by specifying the position of the arm gantry 2 and that of the patient on the examination room coordinates. At this time, the object position specifying unit 433 specifies the position and direction of the patient based on an examination room image. The direction of the patient includes even the posture of the patient. More specifically, the object position specifying unit 433 specifies the positions of feature points of the patient from each of a plurality of examination room images. The feature points can be any regions such as the face, shoulder, arm, and leg of the patient. Based on the positions of the plurality of feature points of the patient in the examination room images, the object position specifying unit 433 can specify the position of the patient on the examination room coordinates and the direction of the patient. Since the positions of the arm gantry 2 and top gantry 3 on the examination room coordinates have already been specified, the position specifying unit 43 can specify the positional relationship between the arm gantry 2 and the patient. In other words, the position specifying unit 43 can specify the positional relationship between the examination room coordinate system, the machine coordinate system, the top coordinate system, and the clinical coordinate system.

The second method is a method of specifying the positional relationship between the arm gantry 2 and a patient by specifying the position and direction of the patient on the top coordinates. At this time, the object position specifying unit 433 specifies the position and direction of the patient on the top 31 based on an output from each of a plurality of pressure sensors 400 arranged on a mat spread on the top 31. More specifically, based on outputs from the plurality of pressure sensors 400, the object position specifying unit 433 detects the positions (head, shoulder, elbow, hip, and heel) of the patient that contact the mat. From this, the object position specifying unit 433 can specify the position and direction of the patient on the top coordinates. In other words, the object position specifying unit 433 can specify the positional relationship between the top gantry 3 and the patient. The positional relationship between the arm gantry 2 and the top gantry 3 has already been known. Thus, the position specifying unit 43 can specify the positional relationship between the arm gantry 2 and the patient. In other words, the position specifying unit 43 can specify the positional relationship between the examination room coordinate system, the machine coordinate system, the top coordinate system, and the clinical coordinate system.

FIG. 17A is a view showing the first example of the positional relationship between the clinical coordinate system and the top coordinate system. As shown in FIG. 17A, assume that it is specified that a patient is placed on his/her back on the top 31 with the body axis parallel to the long axis of the top 31. At this time, the clinical coordinate system and the top coordinate system have a positional relationship shown in FIG. 17A. The front direction (axis Y4) in the clinical coordinate system becomes parallel to the axis Y2 of the top coordinate system. The body axis (axis Z4) of the patient in the clinical coordinate system becomes parallel to the long axis (axis Z2) of the top 31. The clinical angles are assigned as shown in FIG. 17A.

Figure 17B:
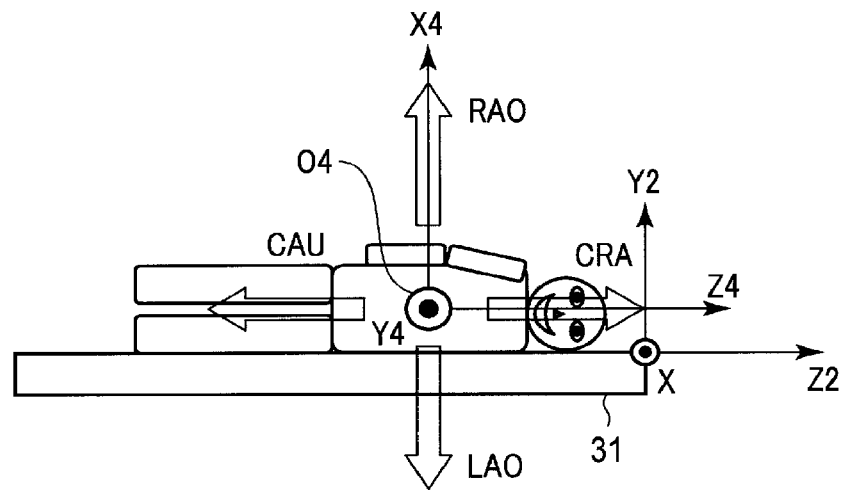
FIG. 17B is a view showing the second example of the positional relationship between the clinical coordinate system and the top coordinate system.

FIG. 17B is a view showing the second example of the positional relationship between the clinical coordinate system and the top coordinate system. As shown in FIG. 17B, assume that it is specified that a patient is placed on his/her side on the top 31 with the body axis parallel to the long axis of the top 31. At this time, the clinical coordinate system and the top coordinate system have a positional relationship shown in FIG. 17B. The front direction (axis Y4) in the clinical coordinate system becomes parallel to the axis X2 of the top coordinate system. The body axis (axis Z4) of the patient in the clinical coordinate system becomes parallel to the long axis (axis Z2) of the top 31. The clinical angles are assigned as shown in FIG. 17B. When the posture of the patient on the top 31 changes, the assignment of the front direction and clinical angles in the clinical coordinate system changes, as shown in FIGS. 17A and 17B. The position specifying unit 43 can specify the positional relationship between a plurality of types of coordinate systems in accordance with a change of the posture of the patient and a change of the orientation in which the patient is placed on the top 31.

A coordinate transformation unit 60 transforms instruction information input in the clinical coordinate system into one in the machine coordinate system based on the positional relationship between the arm gantry 2 and a patient. In other words, the coordinate transformation unit 60 transforms instruction information input in the clinical coordinate system into one in the machine coordinate system based on the positional relationship between the machine coordinate system and the clinical coordinate system. This instruction information includes, e.g., a rotation instruction and a translation instruction for a C-arm 21. The coordinate transformation unit 60 specifies a transformation condition for transforming coordinates in the clinical coordinate system into those in the machine coordinate system. The transformation condition is, e.g., a coordinate transformation matrix.

FIG. 18 is an explanatory view for explaining processing of the coordinate transformation unit 60 of the X-ray diagnostic apparatus according to the third embodiment. In the top coordinate system, the short-axis direction of the top 31 is an X-axis X2, a direction perpendicular to the top surface of the top 31 is a Y-axis Y2, and the long-axis direction is a Z-axis Z2. The origin of the top coordinate system is, e.g., a position shown in FIG. 18. In the machine coordinate system, the X-axis is an axis X1 parallel to a rotation axis Rb, the Z-axis is an axis Z1 parallel to a rotation axis Ra, and the Y-axis is an axis Y1 perpendicular to the X-axis X1 and the Z-axis Z1. The origin of the machine coordinate system is set at the isocenter. The clinical coordinate system has the axis Y4 parallel to the front direction of a patient, the axis Z4 parallel to the body axis of the patient, and the axis X4 perpendicular to the axes Y4 and Z4. The origin of the clinical coordinate system is, e.g., the position shown in FIG. 18. For descriptive convenience, the origin of the machine coordinate system, that of the top coordinate system, and that of the clinical coordinate system are the position shown in FIG. 18. However, the origin of the clinical coordinate system is a fluctuation point such as the imaging center position of an object. The origins of the remaining coordinate systems can also be set arbitrarily. In this case, each of the three axial directions in the machine coordinate system, the three axial directions in the top coordinate system, and the three axial directions in the clinical coordinate system needs to be determined in advance in the respective apparatuses. In other words, the three axial directions serving as a reference for operating the arm gantry 2 are fixed with reference to a predetermined position of the arm gantry 2. The three axial directions serving as a reference for operating the top gantry 3 are fixed with reference to a predetermined position of the top gantry 3. The three axial directions of the clinical coordinate system are those shown in FIG. 16.

An interference data generation unit 45 generates interference data representing the positional relationship between the arm gantry 2 and a patient. More specifically, the interference data includes position data of each of a plurality of mechanisms constituting the arm gantry 2 on the examination room coordinates, and position data of the patient on the examination room coordinates. The interference data may be data representing a distance and direction to the patient from each of the plurality of mechanisms constituting the arm gantry 2. The interference data is data used to limit the moving range of the arm gantry 2. By limiting the moving range of the arm gantry 2, contact of the arm gantry 2 with the patient can be prevented. Therefore, the interference data may be data representing the movable range of the arm gantry 2.

An imaging control unit 50 outputs, to an arm control unit 501, instruction information transformed into the machine coordinate system by the coordinate transformation unit 60.

Figure 18A:
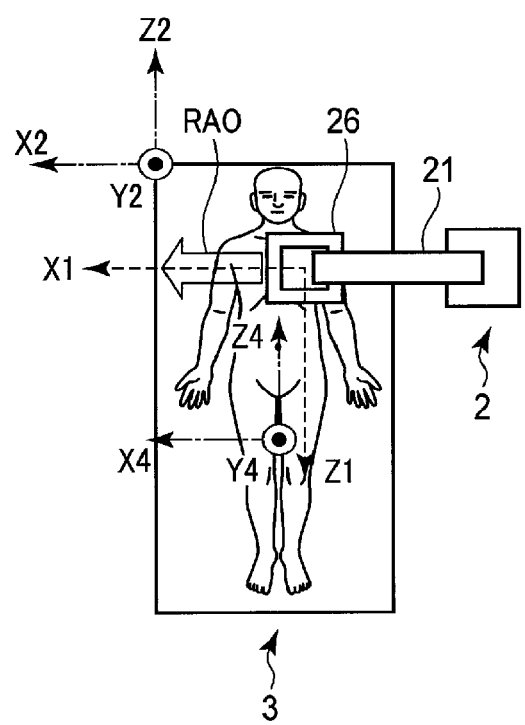
FIG. 18A is a view schematically showing a state in which the C-arm is inserted from the short-axis direction of the top on which a patient is placed.

FIG. 18A is a view schematically showing a state in which the C-arm 21 is inserted from the short-axis direction of the top 31 on which a patient is placed.

FIG. 18B is a view schematically showing a state in which the position of the patient in FIG. 18A is turned upside down with respect to the top 31.

FIGS. 18A and 18B show postures in which the same region of the patient is imaged. However, the orientation of the patient on the top 31 is different between FIGS. 18A and 18B. In the state of FIG. 18A, the patient is placed on the top 31 so that the orientation of the body axis (Z4) of the patient coincides with the orientation of the long axis (Z2) of the top 31. To the contrary, in the state of FIG. 18B, the patient is placed on the top 31 so that the orientation of the body axis (Z4) of the patient becomes opposite to the orientation of the long axis (Z2) of the top 31. As shown in FIGS. 18A and 18B, for example, orientations of the clinical angle RAO are assigned to opposite directions. Hence, for example, when rotation of RAO 20° in the clinical coordinate system is designated, the imaging control unit 50 and the coordinate transformation unit 60 perform the following processing. Referring to FIG. 18A, the coordinate transformation unit 60 transforms the rotation instruction "RAO 20" input in the clinical coordinate system into one in the machine coordinate system. The transformed movement instruction is "20° about the rotation axis Ra in the +X1 direction". The imaging control unit 50 outputs, to the arm control unit 501, a movement control signal for rotating the C-arm 21 by 20° about the rotation axis Ra in the +X1 direction in the machine coordinate system. Referring to FIG. 17B, the coordinate transformation unit 60 transforms the rotation instruction "RAO 20°"' input in the clinical coordinate system into one in the machine coordinate system. The transformed movement instruction is "20° about the rotation axis Ra in the −X1 direction". The imaging control unit 50 outputs, to the arm control unit 501, a movement control signal for rotating the C-arm 21 by 20° about the rotation axis Ra in the −X1 direction in the machine coordinate system.

By the above-described processing of the imaging control unit 50 and coordinate transformation unit 60, the arm gantry 2 is moved in accordance with a movement instruction input in the clinical coordinate system.

The X-ray diagnostic apparatus according to the third embodiment has the following effects.

The X-ray diagnostic apparatus according to the third embodiment can transform movement instruction information input in the clinical coordinate system into one in the machine coordinate system. The X-ray diagnostic apparatus according to the third embodiment can transform pieces of movement instruction information input in the machine coordinate system, the examination room coordinate system, the top coordinate system, and the clinical coordinate system into those in the other coordinate systems. Therefore, the X-ray diagnostic apparatus according to the third embodiment can move the arm gantry 2 in accordance with movement instruction information input in the clinical coordinate system by the user. For example, even when the C-arm 21 is inserted with respect to a patient from various directions, as shown in FIGS. 18A and 18B, the user can input movement of the arm gantry 2 in the clinical coordinate system. The user can move the arm gantry 2 by only inputting a movement instruction in the clinical coordinate system without concern for the positional relationship of the patient with respect to the top 31. In other words, the X-ray diagnostic apparatus according to the second embodiment can easily move the C-arm 21 to a desired position.

The X-ray diagnostic apparatus including at least the portable C-arm 21 or the portable top 31 according to the third embodiment can easily align an object with respect to an imaging position.

Fourth Embodiment

The first, second, and third embodiments have been explained by exemplifying the X-ray diagnostic apparatus including the portable arm gantry 2 and the portable top gantry 3. However, the above-described first, second, and third embodiments are applicable to even an X-ray diagnostic apparatus including the portable top gantry 3, and an imaging system movable in a predetermined range from a fixing position in an examination room. The fourth embodiment will be explained by exemplifying an X-ray diagnostic apparatus including a portable top gantry 3, and an imaging system movable in a predetermined range from a fixing position in an examination room.

Figure 19:
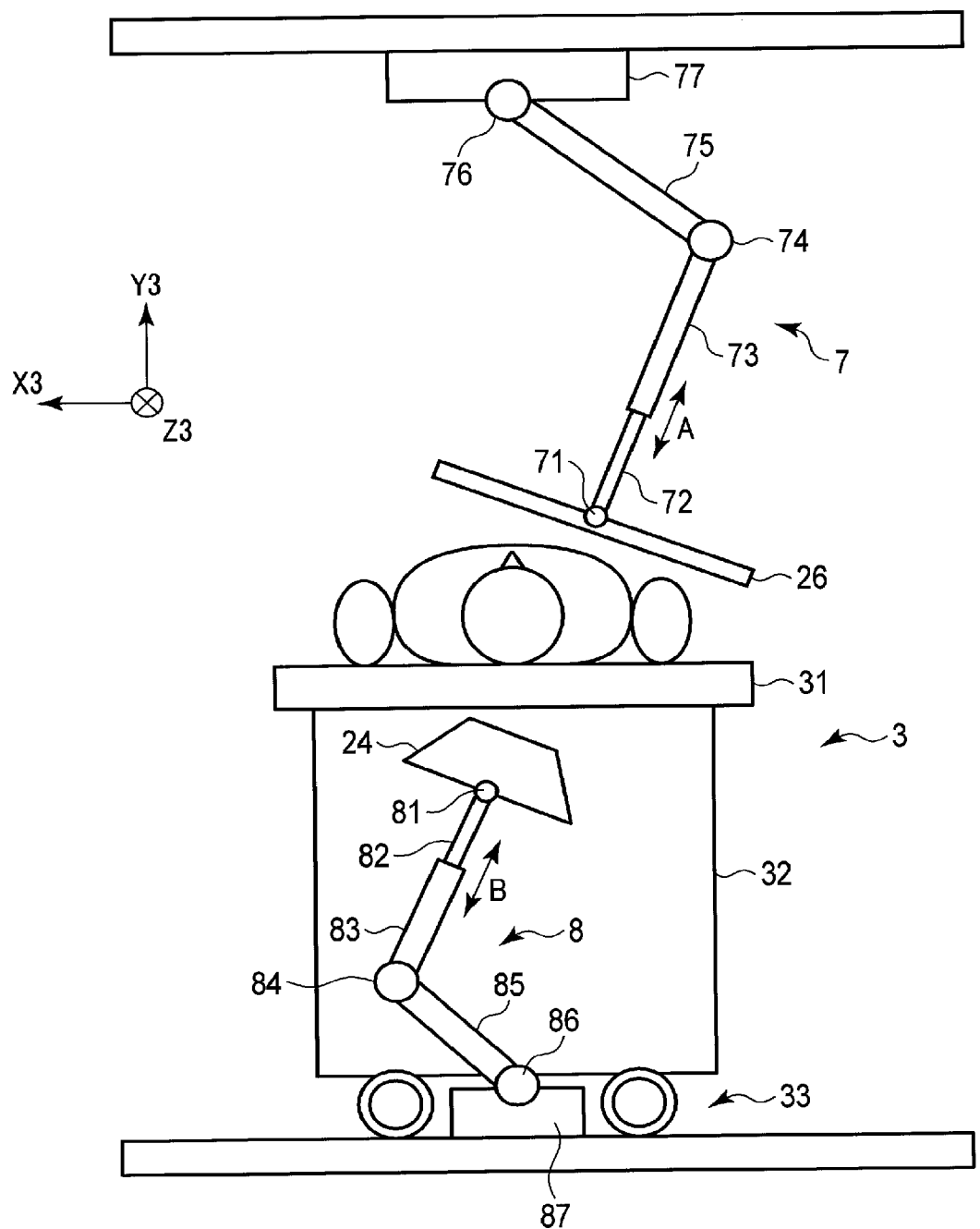
FIG. 19 is a view showing an example of the outer appearance of an X-ray diagnostic apparatus according to the fourth embodiment.

FIG. 19 is a view showing an example of the outer appearance of the X-ray diagnostic apparatus according to the fourth embodiment. As shown in FIG. 19, a holding unit holds the imaging system. The holding unit includes a first holding unit 7 and a second holding unit 8. The first holding unit 7 supports an X-ray detection unit 26 movably in a predetermined range at a fixing position on the ceiling. The second holding unit 8 supports the X-ray detection unit 26 movably in a predetermined range at a fixing position on the floor surface.

The first holding unit 7 includes a suspension base 77, a first suspension arm joint 76, a first suspension arm 75, a second suspension arm joint 74, a second suspension arm 73, a third suspension arm 72, and a third suspension arm joint 71.

The suspension base 77 is fixed to the ceiling. The first suspension arm joint 76 supports the first suspension arm 75 to be freely rotatable with respect to the suspension base 77. The first suspension arm joint 76 has, e.g., a rotation axis parallel to the Z3 axis, and a rotation axis perpendicular to the center line of the first suspension arm 75 and the Z3 axis. The second suspension arm joint 74 supports the second suspension arm 73 to be freely rotatable with respect to the first suspension arm 75. The second suspension arm joint 74 has, e.g., a rotation axis parallel to the Z3 axis, and a rotation axis perpendicular to the center line of the second suspension arm 73 and the Z3 axis. The second suspension arm 73 supports the third suspension arm 72 so as to freely expand/contract it in directions A in FIG. 19. The third suspension arm joint 71 supports the X-ray detection unit 26 to be freely rotatable with respect to the third suspension arm 72. The third suspension arm joint 71 has, e.g., a rotation axis perpendicular to the center line of the third suspension arm 72.

The second holding unit 8 includes a floor surface arm base 87, a first floor surface arm joint 86, a first floor surface arm 85, a second floor surface arm joint 84, a second floor surface arm 83, a third floor surface arm 82, and a third floor surface arm joint 81. The floor surface arm base 87 is fixed to the floor surface. The first floor surface arm joint 86 supports the first floor surface arm 85 to be freely rotatable with respect to the floor surface arm base 87. The first floor surface arm joint 86 has, e.g., a rotation axis parallel to the Z3 axis, and a rotation axis perpendicular to the center line of the first floor surface arm 85 and the Z3 axis. The second floor surface arm joint 84 supports the second floor surface arm 83 to be freely rotatable with respect to the first floor surface arm 85. The second floor surface arm joint 84 has, e.g., a rotation axis parallel to the Z3 axis, and a rotation axis perpendicular to the center line of the second floor surface arm 83 and the Z3 axis. The second floor surface arm 83 supports the third floor surface arm 82 so as to freely expand/contract it in directions B in FIG. 19. The third floor surface arm joint 81 supports an X-ray generation unit 24 to be freely rotatable with respect to the third floor surface arm 82. The third floor surface arm joint 81 has, e.g., a rotation axis perpendicular to the center line of the third floor surface arm 82.

Each of the plurality of joints described with reference to FIG. 19 is independently controlled by driving a driving unit (not shown) under the control of an imaging control unit 50. In accordance with one of the first holding unit 7 and second holding unit 8, the imaging control unit 50 may control the other. As a result, the X-ray generation unit 24 and the X-ray detection unit 26 can face each other. With the arrangement of the first holding unit 7 described above, the X-ray detection unit 26 is supported movably in a predetermined range at the fixing position on the ceiling. With the arrangement of the second holding unit 8, the X-ray generation unit 24 is supported movably in a predetermined range at the fixing position on the floor surface. These predetermined ranges are determined in accordance with the lengths of the respective arms, the rotation directions and rotation ranges of the respective joints, the range of the expansion/contraction operation of the third suspension arm 72 (third floor surface arm 82), and the like.

In the example of FIG. 19, the first holding unit 7 supports the X-ray detection unit 26 movably at the fixing position on the ceiling, and the second holding unit 8 supports the X-ray generation unit 24 movably at the fixing position on the floor surface. However, the fixing positions are arbitrary such as the ceiling, floor, and wall in the examination room as long as the X-ray generation unit 24 and the X-ray detection unit 26 can be supported movably at the fixing positions in the examination room. For example, the first holding unit 7 may support the X-ray detection unit 26 movably at a fixing position on the wall of the examination room, and the second holding unit 8 may support the X-ray generation unit 24 movably at a fixing position on the wall of the examination room.

Alternatively, a common holding unit may support the X-ray generation unit 24 and the X-ray detection unit 26 movably at fixing positions such as the ceiling, floor, and wall in the examination room. The common holding unit may be, e.g., a ceiling suspension type Ω-arm or a C-arm fixed to the wall.

As described in the first embodiment, a position specifying unit 43 can specify the position of the top gantry 3 in the examination room by using an examination room image captured by a camera, a GPS, and an ultrasonic system. By using the same method, the position of the X-ray detection unit 26 and that of the X-ray generation unit 24 in the examination room can be specified.

Note that the position specifying unit 43 can specify the position of each of the X-ray generation unit 24 and X-ray detection unit 26 in the examination room based on an output from the imaging control unit 50. More specifically, the imaging control unit 50 manages the rotation amount of each driving unit from a reference position, its moving amount from the reference position, and the like. Based on an output from the imaging control unit 50, the position specifying unit 43 can specify the position of the X-ray detection unit 26 with respect to the fixing position of the first holding unit 7, and the position of the X-ray generation unit 24 with respect to the fixing position of the second holding unit 8. The position specifying unit specifies the position of the X-ray detection unit 26 in the examination room based on the fixing position of the first holding unit 7 in the examination room, and the position of the X-ray detection unit 26 with respect to the fixing position. Similarly, the position specifying unit specifies the position of the X-ray generation unit 24 in the examination room based on the fixing position of the second holding unit 8 in the examination room, and the position of the X-ray generation unit 24 with respect to the fixing position.

By the above-described processing, the position specifying unit 43 can specify the mechanical positional relationship between the X-ray generation unit 24, the X-ray detection unit 26, and the top gantry 3 based on the positions of the X-ray generation unit 24, X-ray detection unit 26, and top gantry 3 in the examination room. In other words, the position specifying unit 43 can specify the positional relationship between the examination room coordinate system, the top coordinate system, the coordinate system (to be referred to as the first machine coordinate system hereinafter) of the first holding unit 7, and the coordinate system (to be referred to as the second machine coordinates hereinafter) of the second holding unit 8.

The X-ray diagnostic apparatus according to the fourth embodiment can obtain the same effects as those of the X-ray diagnostic apparatus according to each of the first, second, and third embodiments. That is, the X-ray diagnostic apparatus according to the fourth embodiment can automatically move the X-ray generation unit 24, the X-ray detection unit 26, and the top gantry 3 not having undergone intentional alignment to relative positions corresponding to a preset button pressed by the user.

The X-ray diagnostic apparatus according to the fourth embodiment can display an assistant image for manually moving the X-ray generation unit 24, the X-ray detection unit 26, and the top gantry 3 to relative positions corresponding to a preset button. The assistant image includes movement information (moving direction and moving amount) of each of the X-ray generation unit 24, X-ray detection unit 26, and top gantry 3, which is represented by a coordinate system complying with a user instruction. While viewing the assistant image, the user can directly move the top gantry 3 manually and move the X-ray generation unit 24 and the X-ray detection unit 26 by using an operation console.

The X-ray diagnostic apparatus according to the fourth embodiment can transform movement instruction information input in the top coordinate system into those in the first and second machine coordinate systems. More specifically, the X-ray diagnostic apparatus according to the fourth embodiment can transform movement instruction information about the X-ray generation unit 24 that has been input in the top coordinate system, into one in the second machine coordinate system. Also, the X-ray diagnostic apparatus according to the fourth embodiment can transform movement instruction information about the X-ray detection unit 26 that has been input in the top coordinate system, into one in the first machine coordinate system. Accordingly, each of the first holding unit 7 and second holding unit 8 can be moved in accordance with movement instruction information input in the top coordinate system by the user.

In addition, the X-ray diagnostic apparatus according to the fourth embodiment can transform movement instruction information input in the clinical coordinate system into those in the first and second machine coordinate systems. More specifically, the X-ray diagnostic apparatus according to the fourth embodiment can transform movement instruction information about the X-ray generation unit 24 that has been input in the clinical coordinate system, into one in the second machine coordinate system. Also, the X-ray diagnostic apparatus according to the fourth embodiment can transform movement instruction information about the X-ray detection unit 26 that has been input in the clinical coordinate system, into one in the first machine coordinate system. Each of the first holding unit 7 and second holding unit 8 can be moved in accordance with movement instruction information input in the clinical coordinate system by the user.

In short, the X-ray diagnostic apparatus according to the fourth embodiment allows the user to easily perform alignment between the X-ray generation unit 24, the X-ray detection unit 26, and the top gantry.

In summary, the X-ray diagnostic apparatus according to the fourth embodiment can specify the mechanical positional relationship between the X-ray generation unit 24, the X-ray detection unit 26, and the top gantry 3. Alignment between the X-ray generation unit 24, the X-ray detection unit 26, and the top gantry 3 can be easily performed by various methods described above.

The X-ray diagnostic apparatus according to the fourth embodiment including at least the portable C-arm 21 or the portable top 31 can easily align an object with respect to an imaging position.

Some embodiments of the present invention and the modification have been described above. However, the embodiments and modification are presented merely as examples and are not intended to restrict the scope of the invention. These embodiments can be carried out in various other forms, and various omissions, replacements, and alterations can be made without departing from the spirit of the invention. The embodiments and their modifications are also incorporated in the scope and the spirit of the invention as well as in the invention described in the claims and their equivalents.

What is claimed is:

1. An X-ray diagnostic apparatus comprising:
   a bed including a top;
   an X-ray tube configured to generate an X-ray;
   an X-ray detector configured to detect the X-ray which has been generated by the X-ray tube and has passed through an object placed on the top of the bed;
   a holding mechanism configured to hold the X-ray tube and the X-ray detector, and movable on a floor surface of an examination room;
   position specifying circuitry configured to specify a position of the holding mechanism in the examination room and a position of the bed in the examination room; and
   control circuitry configured to control the holding mechanism in order to change the position and an angle of the holding mechanism based on the position of the holding mechanism and the position of the bed, wherein
   the holding mechanism includes:
      an arm holding mechanism configured to rotatably hold the X-ray tube and the X-ray detector, and
      a cart, which is configured to hold the arm holding mechanism movably in the examination room,
   the control circuitry controls at least one of the arm holding mechanism and the cart in order to change the position and an angle of the arm holding mechanism with respect to the too based on the position of the holding mechanism and a plurality of positions on the bed, and
   the control circuitry controls the arm holding mechanism and the cart, which is configured to hold the arm holding mechanism movably in the examination room, in descending order of priority.

2. The X-ray diagnostic apparatus of claim 1, further comprising storage circuitry configured to store data concerning relative positions between the holding mechanism and the bed,
   wherein the control circuitry controls the holding mechanism to change a positional relationship between the holding mechanism and the bed to be a relationship between the relative positions based on the position of the holding mechanism and the plurality of positions on the bed.

3. The X-ray diagnostic apparatus of claim 2, further comprising a plurality of sensors attached to the holding mechanism and a plurality of sensors attached to the bed, wherein the position specifying circuitry specifies the position of the holding mechanism based on outputs from the plurality of sensors attached to the holding mechanism, and specifies the plurality of positions on the bed based on outputs from the plurality of sensors attached to the bed.

4. The X-ray diagnostic apparatus of claim 3, wherein each sensor of the plurality of sensors is a GPS sensor.

5. The X-ray diagnostic apparatus of claim 2, wherein the position specifying circuitry specifies the position of the holding mechanism and the plurality of positions on the bed based on a plurality of images concerning an inside of the examination room that are captured by an external camera that is external to the X-ray diagnostic apparatus.

6. The X-ray diagnostic apparatus of claim 5, wherein the position specifying circuitry specifies a position of an obstacle in the examination room based on the plurality of images concerning the inside of the examination room, and
   the control circuitry limits a moving range of the holding mechanism based on the position of the holding mechanism, the plurality of positions on the bed, and the position of the obstacle.

7. The X-ray diagnostic apparatus of claim 2, wherein the position specifying circuitry specifies a plurality of positions on the object in the examination room, and
   the control circuitry controls the holding mechanism in order to change the position and the angle of the holding mechanism based on the position of the holding mechanism, the plurality of positions on the bed, and the plurality of positions on the object.

8. The X-ray diagnostic apparatus of claim 7, further comprising storage circuitry configured to store data concerning relative positions between the holding mechanism and the object,
   wherein the control circuitry controls the holding mechanism to change a positional relationship between the holding mechanism and the object to be the relative positions based on the position of the holding mechanism and the plurality of positions on the object.

9. The X-ray diagnostic apparatus of claim 7, further comprising a pressure sensor provided on the top, wherein the position specifying circuitry specifies the plurality of positions on the object on the top based on an output from the pressure sensor provided on the top.

10. The X-ray diagnostic apparatus of claim 7, wherein the position specifying circuitry specifies the plurality of positions on the object in the examination room based on a plurality of images concerning an inside of the examination room that are captured by an external camera that is external to the X-ray diagnostic apparatus.

11. The X-ray diagnostic apparatus of claim 2, wherein the position specifying circuitry specifies a positional relationship between a machine coordinate system of the holding mechanism and a top coordinate system of the top by specifying the position of the holding mechanism and the plurality of positions on the bed, and
   the control circuitry controls the holding mechanism in order to change the position and the angle of the holding mechanism based on the positional relationship between the machine coordinate system and the top coordinate system.

12. The X-ray diagnostic apparatus of claim 11, further comprising:
   input circuitry configured to input, in the top coordinate system, a movement instruction to change the position and the angle of the holding mechanism; and
   transformation circuitry configured to transform the movement instruction input in the top coordinate system into a movement instruction in the machine coordinate system based on the positional relationship between the machine coordinate system and the top coordinate system, wherein the control circuitry controls the holding mechanism in accordance with the movement instruction transformed into the machine coordinate system.

13. The X-ray diagnostic apparatus of claim 1, wherein the holding mechanism includes a first holding mechanism configured to movably hold the X-ray detector, and a second holding mechanism configured to movably hold the X-ray tube, and the first holding mechanism and the second holding mechanism are fixed to at least one of a ceiling and a floor in the examination room.

* * * * *